(12) United States Patent
Barnes et al.

(10) Patent No.: US 12,364,781 B2
(45) Date of Patent: Jul. 22, 2025

(54) SYSTEMS AND METHODS FOR DEACTIVATION OF VIRUSES AND OTHER ORGANISMS WITH MOBILE ULTRAVIOLET LIGHT DEVICES

(71) Applicant: Galileo Group, Inc., Tampa, FL (US)

(72) Inventors: Donald Michael Barnes, Tampa, FL (US); Thorsten Mewes, Indialantic, FL (US); James Michael Grichnik, Tampa, FL (US)

(73) Assignee: Galileo Group, Inc., Tampa, FL (US)

( * ) Notice: Subject to any disclaimer, the term of this patent is extended or adjusted under 35 U.S.C. 154(b) by 893 days.

(21) Appl. No.: 17/484,053

(22) Filed: Sep. 24, 2021

(65) Prior Publication Data

US 2022/0088251 A1    Mar. 24, 2022

Related U.S. Application Data

(60) Provisional application No. 63/082,994, filed on Sep. 24, 2020.

(51) Int. Cl.
| | |
|---|---|
| *A61L 2/28* | (2006.01) |
| *A61L 2/10* | (2006.01) |
| *A61L 2/24* | (2006.01) |
| *G06T 7/11* | (2017.01) |

(52) U.S. Cl.
CPC ............ *A61L 2/28* (2013.01); *A61L 2/10* (2013.01); *A61L 2/24* (2013.01); *G06T 7/11* (2017.01); *A61L 2202/16* (2013.01); *A61L 2202/20* (2013.01); *G06T 2207/20084* (2013.01)

(58) Field of Classification Search
CPC ..... A61L 2/28; A61L 2/10; A61L 2/24; A61L 2202/16; A61L 2202/20; A61L 2/26; G06T 7/11; G06T 2207/20084
See application file for complete search history.

(56) References Cited

U.S. PATENT DOCUMENTS

| | | | |
|---|---|---|---|
| 2018/0198993 A1* | 7/2018 | Barnes | H04N 23/51 |
| 2020/0280661 A1* | 9/2020 | Barnes | G06V 10/143 |
| 2021/0112647 A1* | 4/2021 | Coleman | G01S 17/42 |
| 2022/0088251 A1* | 3/2022 | Barnes | A61L 2/24 |
| 2023/0166283 A1* | 6/2023 | Sibley | B05B 15/68 |
| | | | 239/587.5 |
| 2024/0197152 A1* | 6/2024 | Hwang | A61B 1/00055 |
| 2024/0422443 A1* | 12/2024 | Yugawa | G01J 3/10 |

* cited by examiner

*Primary Examiner* — Bobbak Safaipour
(74) *Attorney, Agent, or Firm* — MORGAN, LEWIS & BOCKIUS LLP

(57) ABSTRACT

Provided are mobile imaging devices and methods thereof. A mobile imaging device includes a plurality of light source sets, sensors, and a controller. At least one program is non-transiently stored in and executable by the controller. The program causes the controller to perform a method including acquiring a corresponding value for each condition in a first plurality of conditions when the device is at a first position using the sensors to collect a plurality of measurements associated with a region of interest that is not exposed to the plurality of light source sets. The method includes firing with the device held at the first position, if the corresponding value satisfies a corresponding condition specification for a respective condition in the first plurality of conditions, the plurality of light source sets based on a second plurality of conditions. Accordingly, light emits that is substantially limited to a spectral range.

25 Claims, 14 Drawing Sheets

1300

1302
A method at a mobile imaging device comprising a plurality of light source sets, one or more processors, and a controller. At least one program is non-transiently stored in the controller and executable by the controller, the at least one program causing the controller to perform the method.

1304
Firing, with the mobile imaging device held at a first position, in accordance with a determination that each condition in a first plurality of conditions satisfies a corresponding boundary condition specification, the plurality of light source sets, thereby emitting light that is substantially limited to a spectral range associated with the plurality of light source sets on a region of interest for a period of time.

1306
Determining if a corresponding value for each condition in a second plurality of conditions satisfies a corresponding boundary condition specification based upon a plurality of measurements associated with a region of interest. The plurality of measurements is acquired using the one or more sensors.

Figure 13

SYSTEMS AND METHODS FOR DEACTIVATION OF VIRUSES AND OTHER ORGANISMS WITH MOBILE ULTRAVIOLET LIGHT DEVICES

CROSS-REFERENCE TO RELATED APPLICATION

The present Application claims priority to U.S. Provisional Patent Application No. 63/082,994, entitled "Systems and Methods for Deactivation of Viruses and Other Organisms with Mobile Ultraviolet Light Device," filed Sep. 24, 2020, which is hereby incorporated by reference in its entirety.

BACKGROUND

Field

The present disclosure relates to an imaging device. More particularly, the present disclosure relates to systems and method for imaging using a plurality of light sources.

Description of Related Art

In general, ultraviolet B ("UV-B") irradiation and ultraviolet C ("UV-C") irradiation have been shown to have certain disinfection properties when used to illuminate a target area having harmful bacteria or viral organisms. See Casini et al., (2019), "Evaluation of an Ultraviolet C (UVC) Light-Emitting Device for Disinfection of High Touch Surfaces in Hospital Critical Areas," Int. J. Environ. Res. Public Heath, 16(29), pg. 3572; Gritz et al., 1990, "Ultraviolet radiation for the sterilization of contact lenses," CLAO Journal, 16(4), pg. 294. Conventional devices have been applied to various industries that utilize UV-C irradiation for sterilization. For instance, within the medical field, UV-C irradiation devices have been utilized to facilitate sterilization of entire rooms or individual tools. However, these conventional devices are limited to utilization in these environments having gaseous mediums or a vacuum, such as in a hospital room, and cannot be used for other mediums, such as sterilization of a water solution.

Despite the enormous potential for UV-C devices and sterilization, there exists numerous hurdles that prevent such devices from being universally implemented. Crucial to these hurdles is the fact that UV-C irradiation exposure is harmful for users. Fujii et al., 2004, "The Damaging Effect of UV-C Irradiation on Lens α-crystallin," *Mol. Vis.,* 10, pg. 814. For instance, one conventional solution provides UV-C irradiation devices utilized to facilitate sterilization of entire rooms or structures, effectively blasting all visible of surfaces of the room with UV-C irradiation that are within line of sight of these devices. These devices are often large and bulky, requiring significant weight and/or size. Moreover, these devices do not allow a user to be in the same room as the devices when UV-C light is emitted. In other instances, these devices allow the operator of a device to be in the same room when emitting UV-C irradiation, but the operator is required to wear protective garments. Additionally, these larger devices lack mechanism to emit UV-C irradiation from multiple positions in multiple axis. By way of example, these larger devices cannot reach surfaces outside of a line-of-sight of the device, such as surfaces of an aircraft cabin.

Another conventional solution provides smaller, handheld UV-C irradiation devices that act as stand-alone, dedicated sterilization for small areas. Such devices are primal in nature, requiring the user to ensure their own safety without internal guidance or failsafe features. In this way, these devices are unavailable to everyday users lacking special training or oversight. Furthermore, these devices lack mechanisms that ensure a region is sufficiently sanitized by the user. This is particularly true when using conventional devices for removing bacteria or viruses from regions, requiring prolonged exposure to UV-C irradiation. Id.

Thus, prior to the present disclosure there existed a need for a mobile imaging device that allows for targeted sterilization with UV-C irradiation and having failsafe features that protect users of the mobile device. Furthermore, there existed a need for a mobile imaging device that allows for failsafe features that ensure sterilization of a region of interest with UV-C irradiation.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY

Advantageously, the systems, methods, and mobile imaging devices detailed in the present disclosure address the shortcomings in the prior art detailed above.

Various aspects of the present disclosure are directed to providing a mobile imaging device, non-transitory computer including at least one executable program, and a method thereof.

One aspect of the present disclosure provides a method that is performed at a mobile imaging device. The mobile imaging device includes a plurality of light source sets, one or more sensors, a controller and memory. At least one program is non-transiently stored in the memory and executable by the controller. The at least one program causes the controller to perform the method. The method includes acquiring a corresponding value for each boundary condition in a first plurality of boundary conditions when the mobile imaging device is at a first position based upon a plurality of measurements associated with a region of interest (ROI) that is not exposed to the plurality of light source sets during the acquiring using the one or more sensors. The method includes firing, with the mobile imaging device held at the first position, the plurality of light source sets based on a plurality of firing conditions. The firing is in accordance with a determination that the acquired value of each boundary condition in the first plurality of boundary conditions satisfies a corresponding boundary specification. From this, the imaging device emits light that is substantially limited to a spectral range associated with the plurality of light source sets.

In some embodiments, the one or more sensors includes a gyroscope, an accelerometer, or both.

In some embodiments, the one or more sensors includes an objective lens and a two-dimensional pixelated detector in communication with the objective lens.

In some embodiments, the mobile imaging device further includes an objective lens in optical communication with the detector.

In some embodiments, the plurality of light source sets is distributed in an array about the objective lens. In some embodiments, the array is a polygonal array or a radial array.

In some embodiments, the plurality of firing conditions includes a resolution of an imaged captured though the objective lens.

In some embodiments, the acquiring includes acquiring a first image through the objective lens. Moreover, the firing includes acquiring a second image through the objective lens. In addition, the plurality of firing conditions includes an evaluation the second image based on the first image.

In some embodiments, the first plurality of boundary conditions includes a position tolerance of the mobile imaging device.

In some embodiments, the position tolerance of the mobile imaging device includes one or more translational position tolerances of the mobile imaging device, one or more rotational position tolerances of the mobile imaging device, or both.

In some embodiments, the one or more translational position tolerances includes a height from the region of interest in a range between 2 inches and 15 inches.

In some embodiments, the plurality of firing conditions includes a second position of the mobile imaging device based on the first position of the mobile imaging device.

In some embodiments, the second position of the mobile imaging device consists of one or more rotational positions of the mobile imaging device, a vertical translational position of the mobile imaging device, or both.

In some embodiments, the spectral range is in between 250 nanometers (nm) and 315 nm. In some embodiments, the spectral range is in between 260 nm to 270 nm. In some embodiments, the spectral range is in between 280 nm to 315 nm. In some embodiments, the spectral range is in between 290 nm to 310 nm.

In some embodiments, the firing further includes, in accordance with a determination that the acquired corresponding value of a respective condition in the plurality of boundary conditions does not satisfy the corresponding boundary condition specification, discontinuing firing to the plurality of light source sets.

In some embodiments, the plurality of firing conditions includes an exposure time for emitting light from the plurality of lights.

In some embodiments, the exposure time is in between 5 seconds to 15 seconds. In some embodiments, the exposure time is equal to or greater than 5 seconds.

In some embodiments, the exposure time provides a dosage of approximately 5 milliJoules per square centimeter ($mJ/cm^2$), approximately 25 $mJ/cm^2$, approximately 50 $mJ/cm^2$, approximately 75 $mJ/cm^2$, approximately 100 $mJ/cm^2$, approximately 125 $mJ/cm^2$, or a combination thereof.

In some embodiments, the region of interest includes one or more active organisms.

In some embodiments, the mobile imaging device includes a power supply powering the mobile imaging device and the plurality of light source sets.

In some embodiments, the one or more active organisms includes one or more viruses, one or more bacteria, or both.

In some embodiments, the firing causes the one or more active organisms to become inactive.

Yet another aspect of the present disclosure is directed to providing a method at a mobile imaging device. The mobile imaging device includes a plurality of light source sets, one or more sensors, a controller, and a memory. At least one program is non-transiently stored in the memory and executable by the controller. The at least one program causing the controller to implement processing that includes firing, with the mobile imaging device held at a first position, in accordance with a determination that each condition in a first plurality of conditions satisfies a corresponding condition specification, the plurality of light source sets. This firing emits light that is substantially limited to a spectral range associated with the plurality of light source sets on a region of interest for a period of time. Furthermore, the at least one program causes the controller to implement processing that includes determining if a corresponding value for each condition in a second plurality of conditions satisfies a corresponding condition specification based upon a plurality of measurements associated with a region of interest. The plurality of measurements is acquired using the one or more sensors.

In some embodiments, the plurality of measurements includes a distance between the mobile imaging device and a portion of the region of interest.

In some embodiments, the distance between the mobile imaging device and the portion of the region of interest comprises a depth of the region of interest.

In some embodiments, the plurality of measurements includes an angle of incidence of light on the region of interest.

In some embodiments, the plurality of measurements include a fluence of light at a portion of the region of the interest.

In some embodiments, the plurality of measurements includes an integral of the fluence and the period of time at the portion of the region of interest.

In some embodiments, the determining if the corresponding value for each condition in the second plurality of conditions satisfies a corresponding condition utilizes an evaluation model including a decision tree evaluation model, a neural network evaluation model, a support vector machine evaluation model, a Naïve Bayes evaluation model, a pattern-matching evaluation model, a Bayesian evaluation model, a rule based evaluation model, or a combination thereof.

The mobile imaging device, imaging device, method and non-transitory computer readable storage medium of the present invention have other features and advantages that will be apparent from, or are set forth in more detail in, the accompanying drawings, which are incorporated herein, and the following Detailed Description, which together serve to explain certain principles of exemplary embodiments of the present invention.

BRIEF DESCRIPTION OF THE DRAWINGS

FIG. 13 illustrates a second flow chart of methods for utilizing a mobile imaging device using a device in accordance with an embodiment of the present disclosure.

Figure 1:
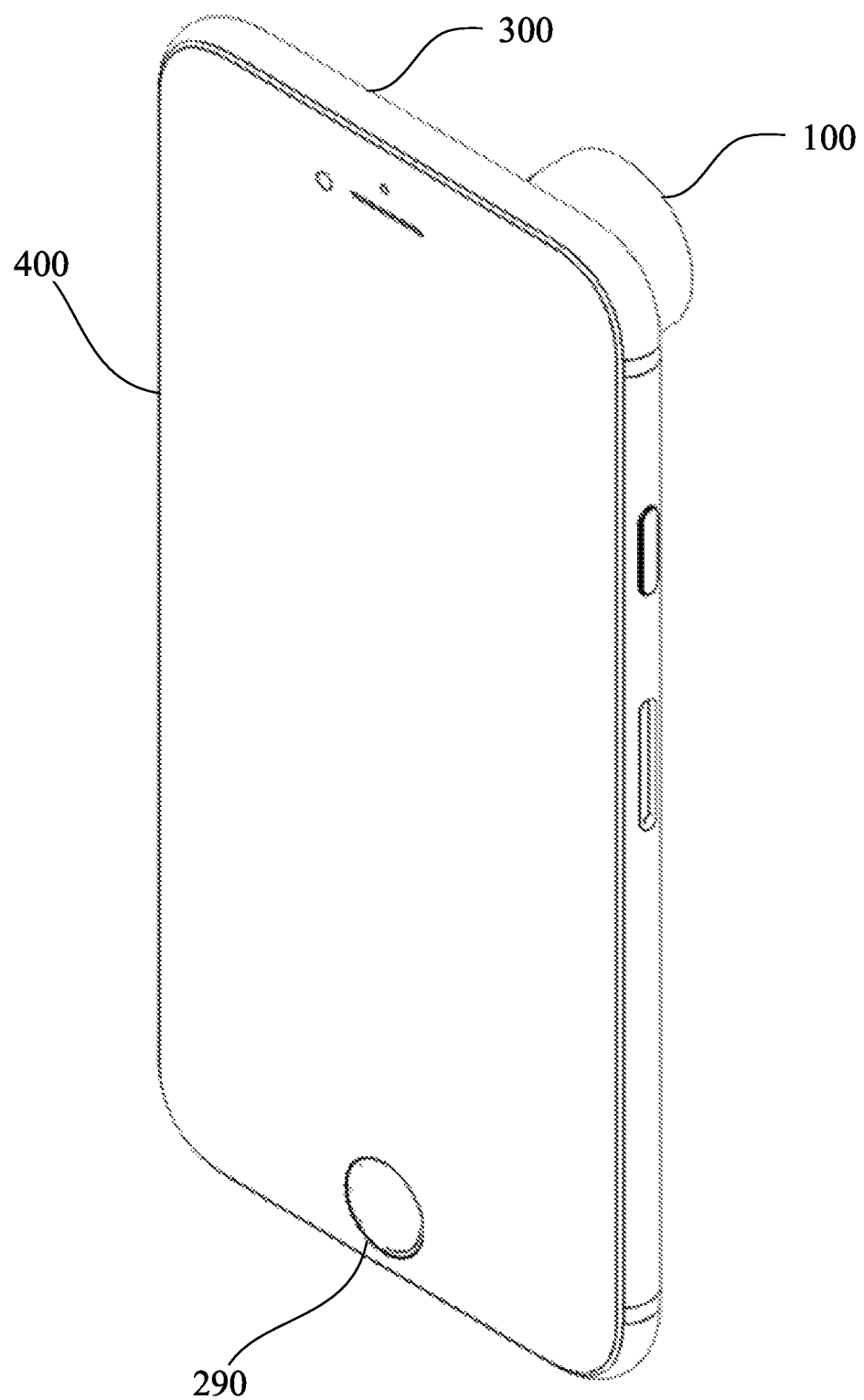
FIG. 1 is an isometric view of a mobile imaging device according to an exemplary embodiment of the present disclosure.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

The present disclosure provides a mobile imaging device and a method thereof. The mobile imaging device includes a plurality of light source sets, one or more sensors, and a controller. At least one program is non-transiently stored in the controller and executable by the controller. The at least one program causes the controller to perform the method. From this, the mobile imaging device of the present disclosure provides a controlled emission of light from the plurality of light source sets through the controller. Moreover, the mobile imaging device provides a determination if the controlled emission of light from the plurality of light source sets satisfies one or more conditions, ensuring that a dosage of light on a region of interest is adequate to sterilize the region of interest. Specifically, the method includes acquiring a corresponding value for each boundary condition in a first plurality of boundary conditions when the mobile imaging device is at a first position, based upon a plurality of measurements associated with a region of interest that is acquired using the one or more sensors of the mobile imaging device. These sensors include an objective lens, an accelerometer, a gyroscope, or a combination thereof. In some embodiments, the region of interest is not exposed to the plurality of light source sets when acquiring the corresponding value for each boundary condition in the first plurality of boundary conditions. In this way, the method provides an envelope of initial conditions for emitting light from the plurality of light source sets. The method includes firing the plurality of light source sets based on a plurality of firing conditions with the mobile imaging device held at the first position. In some embodiments, a respective condition is configured for a predetermined region of interest. This firing of the plurality of light source sets is conducted if the acquired corresponding value of each boundary condition in the first plurality of boundary conditions satisfies a corresponding boundary condition specification. From this, the mobile imaging device emits light that is substantially limited to a spectral range associated with the plurality of light source sets, such as ultraviolet C (UV-C) and/or ultraviolet B (UV-B) light.

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents, and other embodiments, which may be included within the spirit and scope of the invention as defined by the appended claims.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject" and "user" are used interchangeably herein. Additionally, a first light source set could be termed a second light source set, and, similarly, a second light source set could be termed a first light source set, without departing from the scope of the present disclosure. The first light source set and the second light source set are both light source sets, but they are not the same light source set.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Furthermore, when a reference number is given an "$i^{th}$" denotation, the reference number refers to a generic component, set, or embodiment. For instance, a light source set termed "light source set 110-$i$" refers to the $i^{th}$ in a plurality of light source sets.

Moreover, as used herein, the term "parameter" refers to any coefficient or, similarly, any value of an internal or external element (e.g., a weight and/or a hyperparameter) in an algorithm, model, regressor, and/or classifier that can affect (e.g., modify, tailor, and/or adjust) one or more inputs, outputs, and/or functions in the algorithm, model, regressor and/or classifier. For example, in some embodiments, a parameter refers to any coefficient, weight, and/or hyperparameter that can be used to control, modify, tailor, and/or adjust the behavior, learning, and/or performance of an algorithm, model, regressor, and/or classifier. In some instances, a parameter is used to increase or decrease the influence of an input (e.g., a feature) to an algorithm, model, regressor, and/or classifier. As a nonlimiting example, in some embodiments, a parameter is used to increase or decrease the influence of a node (e.g., of a neural network), where the node includes one or more activation functions.

Assignment of parameters to specific inputs, outputs, and/or functions is not limited to any one paradigm for a given algorithm, model, regressor, and/or classifier but can be used in any suitable algorithm, model, regressor, and/or classifier architecture for a desired performance. In some embodiments, a parameter has a fixed value. In some embodiments, a value of a parameter is manually and/or automatically adjustable. In some embodiments, a value of a parameter is modified by a validation and/or training process for an algorithm, model, regressor, and/or classifier (e.g., by error minimization and/or backpropagation methods). In some embodiments, an algorithm, model, regressor, and/or classifier of the present disclosure includes a plurality of parameters. In some embodiments, the plurality of parameters is n parameters, where: $n \geq 2$; $n \geq 5$; $n \geq 10$; $n \geq 25$; $n \geq 40$; $n \geq 50$; $n \geq 75$; $n \geq 100$; $n \geq 125$; $n \geq 150$; $n \geq 200$; $n \geq 225$; $n \geq 250$; $n \geq 350$; $n \geq 500$; $n \geq 600$; $n \geq 750$; $n \geq 1,000$; $n \geq 2,000$; $n \geq 4,000$; $n \geq 5,000$; $n \geq 7,500$; $n \geq 10,000$; $n \geq 20,000$; $n \geq 40,000$; $n \geq 75,000$; $n \geq 100,000$; $n \geq 200,000$; $n \geq 500,000$; $n \geq 1 \times 10^6$; $n \geq 5 \times 10^6$; or $n \geq 1 \times 10^7$. In some embodiments n is between 10,000 and $1 \times 10^7$, between 100,000 and $5 \times 10^6$, or between 500,000 and $1 \times 10^6$.

Various aspects of the present disclosure are directed to providing a mobile imaging device, a non-transitory computer readable storage medium including instructions for one or more programs to operate one or more light source sets of the mobile imaging device, and a method thereof.

While some embodiments of the present disclosure are described in the context of ultraviolet C spectral bands of the electromagnetic spectrum, one skilled in the art will appreciated that other spectral bands of the electromagnetic spectrum can also be utilized by the present disclosure. For instance, in some embodiments, the present disclosure is utilized with ultraviolet C spectral bands, ultraviolet B spectral bands, or both. However, the present disclosure is not limited thereto.

A mobile imaging device of the present disclosure can be utilized in a plurality of fields and industries. In one implementation, an imaging device can be utilized for medical and/or sterilization purposes, such as personal-use, close range object sterilization applications (e.g., sterilization of a property belonging to a user), and/or industrial sterilization purposes (e.g., as a component of a clean-room environment), and the like. Cases can vary from regions of interest as small as tens or hundreds of microns such as an organism or virus, to regions of interest of approximately 500 square centimeters ($cm^2$) for uses such as object and tool sterilization (e.g., sterilization of an office desk and computer station), and even to regions of interest on a scale of tens or hundreds of square meters ($m^2$). Regions of interest in science and sterilization cases can range from 1 square meter ($m^2$) or less, such a bed, to hundreds of square meters such as a structure. In such large region of interest cases, an array of mobile imaging devices can be utilized and/or a single mobile imaging device. Additionally, regions of interest include two-dimensional regions of interest (e.g., a surface of an object), three-dimensional regions of interest (e.g., a volumetric region such as a volume of a solution), and four-dimensional regions of interest (e.g., a volumetric region including a temporal dimension). By way of example, in some embodiments, the three-dimensional regions in interest include a solution (e.g., in an open container) having a depth. In some embodiments, the depth of the region of interest in between 0.5 millimeter (mm) and 250 mm, between 0.5 mm and 150 mm, between 0.5 mm and 100 mm, between 1 mm and 50 mm, between 5 mm and 25 mm, between 5 mm and 20 mm, between 5 mm and 15 mm, between 7.5 mm and 12.5 mm (e.g., 10 mm), or a combination thereof. Additional details and information regarding the use of three- and four-dimensional regions of interest can be found at Kuo et al., 2003, "Standardized Collimated Beam Testing Protocol for Water/Wastewater UItraviolet Disinfection," Journal of Environmental Engineer, 129(8), pg. 774; Tchobanoglous et al., 2003, "Wastewater Engineering: Treatment and Reuse," Metcalf and Eddy Inc., 4, print, each of which is hereby incorporated by reference in its entirety.

FIG. 1 illustrates an exemplary embodiment of an imaging device 100, a housing 300 having an exterior and an interior, and a mobile imaging device 400. In the present embodiment, the housing 300 is attached to the mobile imaging device 400. In such embodiments, the housing 300 typically snap fits to the mobile imaging device 400. However, the present disclosure is not limited thereto. In some embodiments, the housing 300 is integrated, or embedded, with the mobile imaging device 400.

Figure 2:
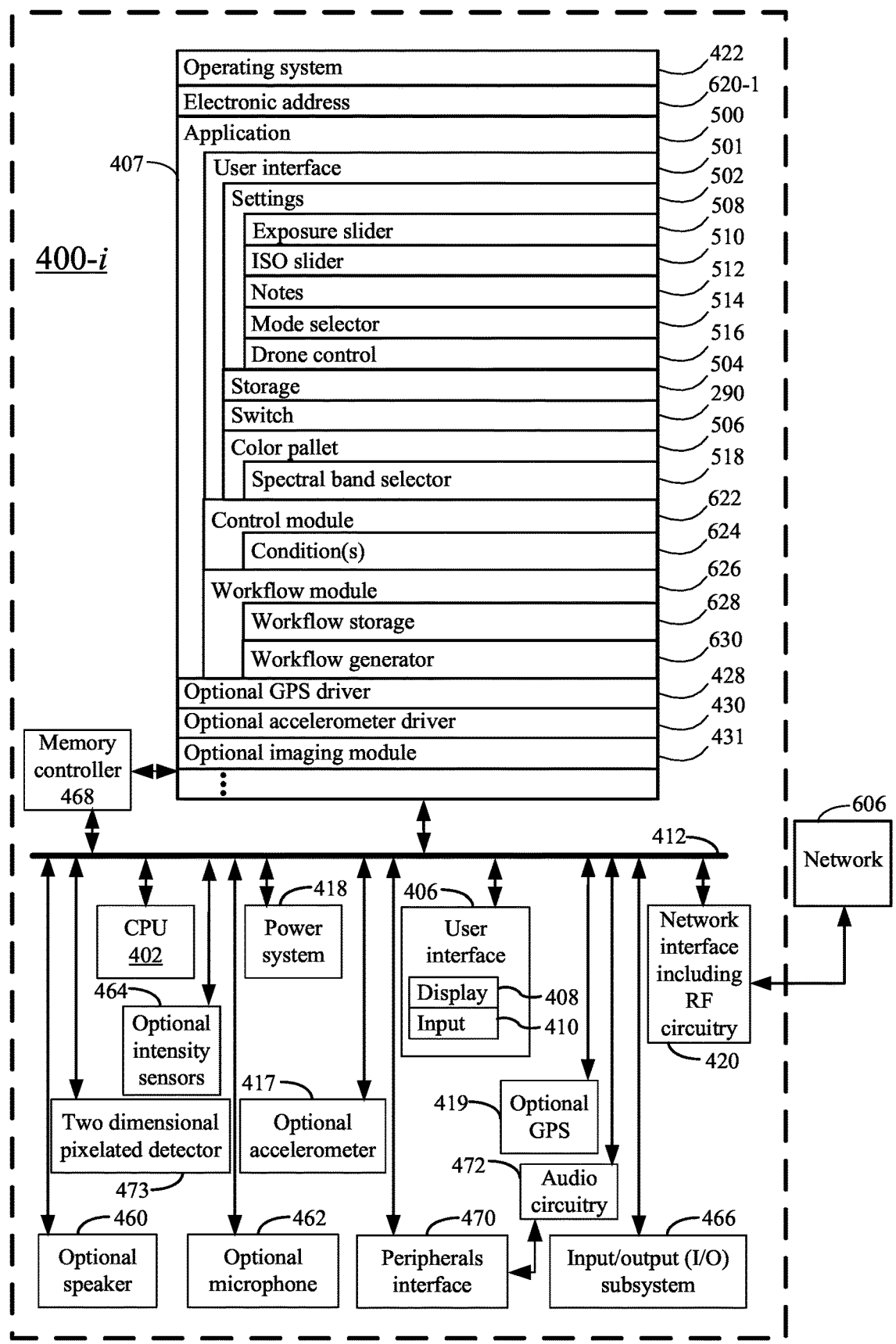
FIG. 2 illustrates a mobile imaging device associated with an imaging device according to an exemplary embodiment of the present disclosure.

FIG. 2 provides a description of a mobile imaging device 400 that can be used with the present disclosure. The mobile imaging device 400 has one or more processing units (CPU's) 402, peripherals interface 470, memory controller 468, a network or other communications interface 420, a memory 407 (e.g., random access memory), a user interface 406, the user interface 406 including a display 408 and input 410 (e.g., keyboard, keypad, touch screen), an optional accelerometer 417, an optional GPS 419, optional audio circuitry 472, an optional speaker 460, an optional microphone 462, one or more optional intensity sensors 464 for detecting intensity of contacts on the device 102 (e.g., a touch-sensitive surface such as a touch-sensitive display system 408 of the device 102), optional input/output (I/O) subsystem 466, one or more communication busses 412 for interconnecting the aforementioned components, and a power system 418 for powering the aforementioned components.

In some embodiments, the input 410 is a touch-sensitive display (e.g., display 408 of FIG. 2), such as a touch-sensitive surface. In some embodiments, the user interface 406 includes one or more soft keyboard embodiments. The soft keyboard embodiments may include standard (QWERTY) and/or non-standard configurations of symbols on the displayed icons. In some embodiments, the mobile imaging device 400 further includes a display 408, and the method further includes displaying information on the display 408, such as one or more boundary conditions and/or firing conditions (e.g., conditions 624 of FIG. 2) or an image captured by the mobile imaging device 400. In some embodiments, the displayed image is enlargeable or reducible by human touch to the touch screen display 408. In some embodiments, the display 408 is configured for focusing an image of a surface of a region of interest acquired by the two-dimensional pixelated detector. Furthermore, in some embodiments, the display 408 allows for the user to visualize the region of interest when directly viewing the region of interest is undesirable for the user, such as if the region of interest is exposed to ultraviolet C irradiation (e.g., from the plurality of light source sets 110). Additionally, in some embodiments, the display allows the user to visual the region of interest when the region of interest is otherwise out of the line of sight of the user, such as around a corner or behind an object. However, the present disclosure is not limited thereto.

The mobile imaging device 400 includes one or more sensors, such as one or more accelerometers 417 and/or one or gyroscopes, and, optionally, includes, a magnetometer and a GPS 419 (or GLONASS or other global navigation system) receiver for obtaining information concerning a position of the mobile imaging device 400, such as a location and/or an orientation (e.g., portrait or landscape; orientation with respect to one or more axis; a pose) of the mobile imaging device 400. In this way, one or more changes in the positioning of the mobile imaging device 400 can be determined through the measurements of positions obtained from the one or more sensors of the mobile imaging device 400, such as if the mobile imaging device 400 is held at a first position. Accordingly, in some embodiments, the mobile imaging device 400 places one or more boundary and/or firing conditions 624 that is based on the one or more changes in positioning of the mobile imaging device 400, which is determined from the one or more sensors of the mobile imaging device 400 (e.g., accelerometer 417, gyroscope, GPS 419, objective lens 210, or a combination thereof). From this, the mobile imaging device 400 can discontinue (i.e., cease) firing of the plurality of light source sets 110 and/or instruct for further firing of the plurality of light source sets 110 when the changes in the positioning of the mobile imaging device 400 do not satisfy the boundary and/or firing conditions 624. However, the present disclosure is not limited thereto. In some embodiments, a plurality of measurements obtained from the one or more sensors of the mobile imaging device 400 includes a corresponding value for one or more conditions 624, such as each boundary condition 624 or a subset of boundary conditions 624. Additionally, in some embodiments, the plurality of measurements and/or one or more characteristics associated with a corresponding firing of the plurality of light source sets 110 is stored in a memory of the mobile imaging device 400 (e.g., workflow storage 628 of memory 407 of FIG. 2). This storing at least allows for the mobile imaging device 400 to provide an evaluation a previous instance of firing the plurality of light source sets 110 and/or a template workflow for repeating the previous instance of firing the plurality light source sets 110. However, the present disclosure is not limited thereto.

It should be appreciated that the mobile imaging device 400 is only one example of a multifunction device that may be used by users when engaging with an imaging device 100, and that the mobile imaging device 400 optionally has more or fewer components than shown, optionally combines two or more components, or optionally has a different configuration or arrangement of the components. The various components shown in FIG. 2 are implemented in hardware, software, firmware, or a combination thereof, including one or more signal processing and/or application specific integrated circuits.

Memory 407 optionally includes high-speed random access memory and optionally also includes non-volatile memory, such as one or more magnetic disk storage devices, flash memory devices, or other non-volatile solid-state memory devices. Access to the memory 407 by other components of the mobile imaging device 400, such as the CPU(s) 402 is, optionally, controlled by a memory controller 468.

In some embodiments, a peripherals interface 470 can be used to couple input and output peripherals of the mobile imaging device 400 to the CPU(s) 402 and the memory 407. The one or more processors 402 run or execute various software programs and/or sets of instructions stored in the memory 407 to perform various functions for the mobile imaging device 400 and to process data. For instance, in some embodiments, the various software programs and/or set of instructions (e.g., application 500 of FIG. 2) allows for a controlled firing of the plurality of light source sets 110. In some embodiments, this controlled firing is based on one or more predetermined conditions 624 or user defined conditions 624. However, the present disclosure is not limited thereto.

In some embodiments, the peripherals interface 470, the CPU(s) 402, and the memory controller 468 are, optionally, implemented on a single chip. In some other embodiments, the peripherals interface 470, the CPU(s) 402, and the memory controller 468 are, optionally, implemented on separate chips.

The RF (radio frequency) circuitry 420 of network interface 420 receives and sends RF signals, also called electromagnetic signals. The RF circuitry 420 converts electrical signals to/from electromagnetic signals and communicates with communications networks and other communications devices via the electromagnetic signals. The RF circuitry 420 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. Moreover, the RF circuitry 420 optionally communicates with the network 606. In some embodiments, network circuitry does not include the RF circuitry and, in fact, is connected to the network 606 through one or more hard wires (e.g., an optical cable, a coaxial cable, or the like).

Examples of the network 606 includes, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSDPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

In some embodiments, an audio circuitry 472, a speaker 460, and a microphone 462 provide an audio interface between a user and the mobile imaging device 400. The audio circuitry 472 receives audio data from the peripherals interface 470, converts the audio data to an electrical signal, and transmits the electrical signal to the speaker 460. The speaker 460 converts the electrical signal to human-audible sound waves. The audio circuitry 472 also receives electrical signals converted by the microphone 462 from sound waves. The audio circuitry 472 converts the electrical signal to audio data and transmits the audio data to the peripherals interface 470 for processing. The audio data is, optionally, retrieved from and/or transmitted to the memory 407 and/or the RF circuitry 420 by the peripherals interface 470. In some embodiments, the speaker 460 is utilized to communicate one or more audible instructions associated with a firing of the plurality of light source sets, such as an instruction to for a user to move the mobile imaging device 400 in a first direction (e.g., away from the region of interest, towards a portion of the region of interest, etc.).

In some embodiments, the power system 418 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management, and distribution of power in portable devices. In some embodiments, such as various embodiments where the housing 300 is integrated with the mobile imaging device 400, a battery 240, a power management circuit 260, and a communication interface 280 can be components of the mobile imaging device 400, such as a power system 418 and a network interface 420. In this way, the mobile imaging device 400 is capable of providing power to the imaging device 100 and the plurality of light source sets 110 through the power system 418 of the mobile imaging device 4000, allowing for a user to fire the plurality of light source sets 110 at a variety of regions of interest without restriction to a wired power supply, such as an electrical outlet, for the imaging device 100. Moreover, by allowing the imaging device 100 to utilize the power system 418 of the mobile imaging device 400, the imaging device 100 can further utilize the sensors of the mobile imaging device 400 without requiring one or more sensors ancillary to the mobile imaging device 400, and power for the one or more sensors, of the imaging device 100 itself. Additionally, in some embodiments, this configuration allows a greater distance and/or angled (i.e., bent) distance to be provided between the mobile imaging device 400 and the imaging device 100, which reduces a level of harm to a user and allows access to difficult to reach regions of interest when utilizing UV-C irradiance with the plurality of light source sets 110.

In some embodiments, the mobile imaging device 400 optionally also includes one or more two-dimensional pixelated detectors 473. The one or more two-dimensional pixelated detector 473 optionally includes a charge-coupled device (CCD), a complementary metal-oxide-semiconductor (CMOS) phototransistors, a photo-cell, and a focal plane array. The two-dimensional pixelated detector 473 receives light from the environment, communicates with one or more lens, such as an objective lens 210, and converts the light to data representing an image. In conjunction with the imaging module 431 (also called a camera module), the two-dimensional pixelated detector 473 optionally captures still images and/or video of a region of interest. In some embodiments, the captured images and/or video for region of interest allows for the mobile imaging device 400 to determine an identity of the region of interest and/or a characteristic associated with the region of interest, such as a reflectance of the region of interest, a size of the region of interest (e.g., a depth of the region of interest, a volume of the region of interest, a surface area of the region of interest, etc.) However, the present disclosure is not limited thereto.

In some embodiments, a first two-dimensional pixelated detector 473-1 is located on a rear end portion of the mobile imaging device 400, opposite a display system 408 on a front end portion of the mobile imaging device 400, so that the touch screen is enabled for use as a viewfinder for still and/or video image acquisition. In some embodiments, a second two-dimensional pixelated detector 473-2 is located on the front end portion of the mobile imaging device 400, allowing for the mobile imaging device 400 to acquire images and/or video of the user when operating the mobile imaging device 400 (e.g., while conducting block 1004 and/or 1006 of FIG. 10). In the exemplary embodiment, a two-dimensional pixelated detector 473 is disposed within the housing 300.

As illustrated in FIG. 2, a mobile imaging device 400 preferably includes an operating system 422 that includes procedures for handling various basic system services. The operating system 422 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments, a mobile imaging device 400 further includes an electronic address 620 (e.g., a mobile phone number, a social media account, an e-mail address, an internet protocol (IP) address, etc.) associated with the corresponding mobile imaging device 400. In such embodiments, an application 500 utilizes the electronic address 620 for communication, such as identifying the mobile imaging device 400 within a communications network 606. In this way, the mobile imaging device 400 can receive specific communications (e.g., specific conditions 624) communicated from a remote device through the electronic address 620 and the communications network 106, such as receiving a predetermined workflow for firing the plurality of light source sets 110.

In some embodiments, meta data is associated with captured multimedia (e.g., images and/or video of a region of interest), such as a device identifier (e.g., identifying the mobile imaging device 400 within a group of mobile imaging devices 400 that captured the multimedia item, which may include an arbitrary identifier, a MAC address, a device serial number, etc.), temporal meta data (e.g., date and time of a corresponding capture), location data (e.g., GPS coordinates of the location at which multimedia item was captured, a position of the mobile imaging device 400, etc.), a multimedia capture frequency (e.g., the frequency at which a stream of images is captured by the mobile imaging device 400), device configuration settings (e.g., image resolution captured multimedia items, frequency ranges that the pixilated detector of the mobile imaging device 400 is configured to detect, one or more boundary conditions 624 and/or one or more firing conditions 624 of the mobile imaging device 400, one or more determinations of satisfying the one or more conditions 624, etc.), and/or other camera data or environmental factors associated with captured multimedia at the mobile imaging device 400.

Accordingly, U.S. Pub. No.: 2017/0323472, entitled "METHODS AND SYSTEMS FOR SURFACE INFORMATICS BASED DETECTION WITH MACHINE-TO-MACHINE NETWORKS AND SMART PHONES," U.S. application Ser. No. 15/521,871, entitled "TEMPORAL PROCESSES FOR AGGREGATING MULTI DIMENSIONAL DATA FROM DISCRETE AND DISTRIBUTED COLLECTORS TO PROVIDE ENHANCED SPACE-TIME PERSPECTIVE," U.S. application Ser. No. 15/522,175, entitled "METHODS AND SYSTEMS FOR REMOTE SENSING WITH DRONES AND MOUNTED SENSOR DEVICES," U.S. application Ser. No. 15/532,578, entitled "SWARM APPROACH TO CONSOLIDATING AND ENHANCING SMARTPHONE TARGET IMAGERY BY VIRTUALLY LINKING SMARTPHONE CAMERA COLLECTORS ACROSS SPACE AND TIME USING MACHINE-TO MACHINE NETWORKS," U.S. application Ser. No. 15/867,653, entitled "SYSTEMS AND METHODS FOR SPECTRAL IMAGING WITH A TRANSMITTER USING A PLURALITY OF LIGHT SOURCES," and U.S. application Ser. No. 16/780,755, entitled "SYSTEMS AND METHODS FOR SPECTRAL IMAGING WITH COMPENSATION FUNCTIONS," are each hereby incorporated by reference in their entirety.

In some embodiments, the mobile imaging device 400 further includes an application 500, which allows for a user of the mobile imaging device 400 to at least control a firing of the plurality of light source sets 110 through a user interface 501 of the application 500 and/or configure a future firing of the plurality of light source sets 110, such as configuring a workflow for firing the plurality of light source sets 110 through a workflow generator 630 of the application 500. However, the present disclosure is not limited thereto. In some embodiments, the application 500 runs on native device frameworks, and is available for download onto one or more mobile imaging devices 400 running an operating system 422, such as an Android operating system 422 or an iOS operating system 422.

In some embodiments, the user interface 501 of the application 500 includes a setting module 502, a gallery or storage 504, the fire or switch 290, a color pallet 506 including Spectral band selector slider 518, or a combination thereof. In some embodiments, the settings 502 opens a menu or table, such as an interface table menu, of various options and customizable parameters to configure when operating the mobile imaging device 400. Such options and parameters include an exposure time slider 508 (e.g., a dosage selector), an ISO light sensitivity slider 510, a notes area 512, a mode selector 514, a remote drone control 516, or a combination thereof.

In some embodiments, the user interface 501 provides a view of an image captured by one or more objective lens 210 of the mobile imaging device 400. By way of example, a first mobile imaging device 400-1 includes a first objective lens 210-1 that faces a first direction, which is a same direction as UV-C irradiation emitted by the plurality of light source sets 110, and a second objective lens 210-2 that faces a second direction opposite the first direction, such as towards a user of the first mobile imaging device 400-1. Accordingly, a user of the first mobile imaging device 400-1 can view the region of interest when UV-C irradiance is emitted from the plurality of light source sets 110 without harming the user, or view the region of interest if outside of the line of sight of the user. Moreover, the first mobile imaging device 400-1 can capture one or more images from the second objective lens 210-2 when the firing of the plurality of light source sets 110 occurs. By way of example, the mobile imaging device 400 can evaluate the one or more images from the second objective lens 210-2 ensuring that the user is facing the second objective lens 210-2, and, therefore, not facing the first objective lens 210-1 or in a region that UV-C irradiation is prone to entering the peripheral vision of the user. However, the present disclosure is not limited thereto.

In some embodiments, the exposure slider 508 allows a user to adjust an exposure time of an image and/or an exposure time for firing (e.g., emitting light from) the plurality of light source sets 110 (e.g., from $\frac{1}{3200}$ of a second to 30 seconds, etc.). In some embodiments, the exposure slider 508 allows the user to adjust an exposure time for firing the plurality of light source sets 110, such that a target dosage of UV-C irradiation at a region of interest is modified, at in part, on the exposure time selected by the exposure slider 508. In some embodiments, an ability for the user to adjust the exposure time for firing the plurality of light source sets 110 is based on one or more conditions 624, such as one or more boundary conditions 248 and/or one or more firing conditions 624. In this way, the exposure slider 5087 provides the user with an envelope of configurable exposure times, such that the user cannot select an exposure time that can harm the user and/or a subject in the region of interest, or cannot select an unreasonable exposure time. However, the present disclosure is not limited thereto.

For instance, in some embodiments, the mobile imaging device 400 determines a characteristic of a region of interest (e.g., a material of a surface of the region of interest, such as a glass surface, a ceramic surface, a metallic surface; a distinctive shape associated with the region of interest; etc.) and modifies an exposure time or a range of exposure times selected through the exposure slider 508 based on the characteristic of the region of interest. In this way, the dosage of UV-C irradiation applied by the mobile imaging device 400 can correspond to various characteristics of the region of interest identified by the mobile imaging device 400. From this, the present disclosure can not only ensure sufficient sterilization of the region of interest, but also reduce a risk of harm to the user through unnecessary firing of the plurality of light source sets 110.

The ISO slider 510 adjusts the ISO of an acquired image. In some embodiments, ISO slider can be adjusted to values in between 50 and 12,800.

A notes 512 module is configured to allow a user of the application 500 to input various text, images, videos, and the like, as well as providing one or more predetermined and/or stored notes for the user. For instance, in some embodiments, the notes 512 module includes one or more predetermined notes associated with a firing of the plurality of light source sets 110 (e.g., block 1006 of FIG. 10). By way of example, in some embodiments, the one or more predetermined notes includes notes associated with satisfying and/or not-satisfying one or more conditions 624 for firing the plurality of light source sets 110. Accordingly, in accordance with a determination that the satisfying and/or not satisfying one or more conditions 624 occurs, the application 500 can display a corresponding predetermined note on the user interface 501 of the display 408 of the mobile imaging device 400, bringing the one or more conditions 624 to the attention of the user. As a non-limiting example, in some embodiments, the one or more conditions includes a first firing conditions 624-1 associated with an unobstructed view of a region of interest (e.g., no objects interposing between a surface of the region of interest and the mobile imaging device 100), such that when the view of the region of interest is obstructed a first predetermined note associated with the first firing condition 624-1 is displayed on the user interface 501 of the display 408 of the mobile imaging device 400, bringing the obstruction to the attention of the user. However, the present disclosure is not limited thereto.

A mode selector 514 allows a user to adjust an acquired image according to various uses cases of the imaging device 100 and/or the mobile imaging device 400, such as selection between a first mode and a second mode. In some embodiments, the selection between one or more modes of the imaging device 100 is determined based on one or more conditions 624 associated with the mobile imaging device 400. In some embodiments, the mode selector 514 allows the user to adjust between a first mode associated with a first spectral range and a second mode associated with a second spectral range, such as a first UV-C mode and a second visible light mode. In some embodiments, the mode selector 514 allows the user to switch between a third mode configured to allow the user to target any region of interest, and a fourth mode configured to allow the user to target one or more predetermined regions of interest. For instance, in some embodiments, the user can select one or more regions of interest before utilizing the mobile imaging device 400, such as regions of interests associated with high rates of bacteria. In some embodiments, the one or more predetermined regions of interest include one or more user defined regions of interests and/or one or more regions of interest from a prior firing of the plurality of light source sets 110. In this way, the mobile imaging device 400 can be restricted to firing the plurality of light source sets 110 towards the one or more predetermined regions of interest. However, the present disclosure is not limited thereto. In some embodiments, the one or more predetermined regions of interest is associated with one or more corresponding boundary conditions 624. For instance, in some embodiments, a first region of interest (e.g., a keyboard, which has number grooves and hidden surfaces) is associated with a first dosage of a boundary condition 624 for emitting UV-C irradiation from the mobile imaging device 400, In some embodiments, a drone control 516 module can be utilized in various embodiments where the imaging device 100 is attached to a drone, such as an unmanned remote demote device, or each mobile imaging device 400 in a plurality of mobile imaging devices 400 is attached to a respective drone in a plurality of drones. However, the present disclosure is not limited thereto. In such embodiments, swarm control and/or control of individual drone and respective devices can be manipulated through the drone control 516. However, the present disclosure is not limited thereto. In some embodiments, the drone control 516 is utilized to operate and/or control the mobile imaging device 400 from a remote location, such that the mobile imaging device 400 acts as a user controlled drone device for a first user at the remote location. In this way, in some embodiments, the drone control 516 module facilities receiving one or more instructions related to a firing of the plurality of light source sets 110, including one or more instructions associated with a condition 624, one or more instructions associated with storing images captured at the mobile imaging device 400, and the like. For instance, in some embodiments, the one or more instructions includes one or more boundary condition specifications.

In some embodiments, a spectral band selector slider 518 module allows a user to manipulate spectral bands of emitted light. In some embodiments, the spectral band selector slider is a standard red, green, blue (RGB) 256-point slider. In this way, a selection of a first light source set 110-1 or a plurality of light source sets 110 is configurable to provide various bands of light emitted by the mobile imaging device. Moreover, in some embodiments the spectral band selector slider 518 allows for a selection of an intensity of light emitted from the first light source set 110-1 or the plurality of light source sets 110. From this, the spectral band selector allows for a selection of a band of electromagnetic light and/or an intensity of light emitted from the plurality of light source sets 110. However, the present disclosure is not limited thereto. In other embodiments, the slider 518 can incorporate other spectral bands of the electromagnetic spectrum including, but not limited to, an infrared light spectral band and/or an ultraviolet light spectral band, specifically the UV-C spectral band. By way of example, in some embodiments, the slider 518-8 allows for the mobile imaging device 400 to emit light through the plurality of light source sets 110 from a first spectral band of ultraviolet C (UV-C) light, a second spectral band of infrared light, a third spectral band of visible light, or a combination thereof. As another non-limiting example, in some embodiments, the slider 518 allows for the mobile imaging device 400 to emit light through the plurality of light source sets 110 from a first spectral band of UV-C light from 260 nm to 265 nm and a second spectral band of UV-C light from 265 nm to 270 nm. However, the present disclosure is not limited thereto. In some embodiments, the mobile imaging device 400 emit light through the plurality of light source sets 110 from a spectral band of ultraviolet B (UV-B) light (e.g., from 290 nm to 310 nm). In some embodiments, these options of the spectral band selector slider 518 are automatically adjusted and optimized according to various environmental factors, or can be manually adjusted by a user of the mobile imaging device 400, or further can be adjusted based one or more conditions 624, such as one or more conditions that is predetermined based on a corresponding region of interest and/or application (e.g., a first condition 624-1 based on a predetermined region of interest associated with a keyboard; a second condition 624-2 based on an application of emitting light at a first medium, such as water or air; etc.). For instance, in some embodiments, the spectral band selector 518 is in communication with a control module (e.g., control module 622) that includes a plurality of conditions (e.g., conditions 624) for utilizing one or more features of the application 500, such as a control of emitting light from the imaging device 100.

Figure 3:
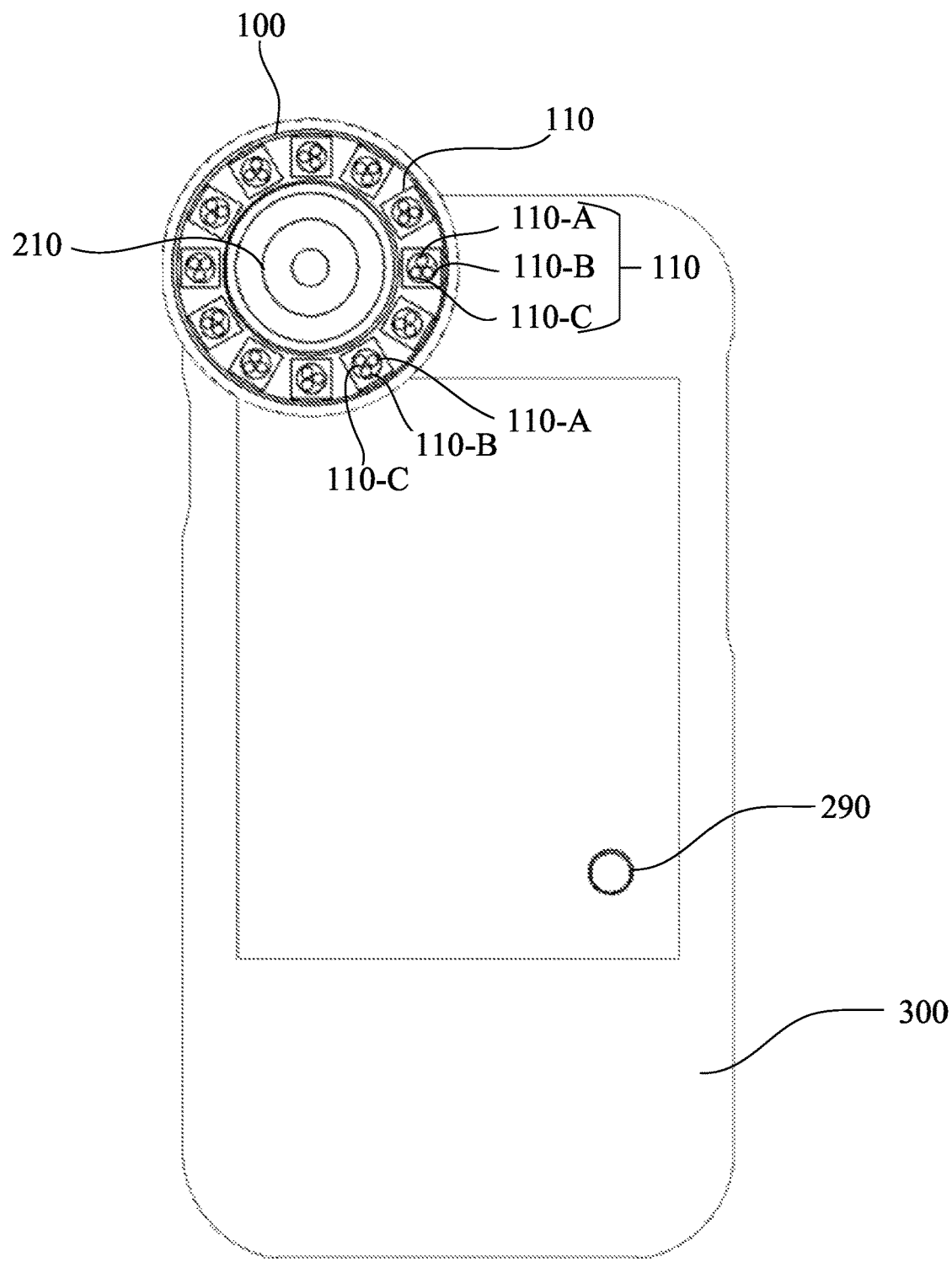
FIG. 3 a front schematic view of a mobile imaging device according to an exemplary embodiment of the present disclosure.

In some embodiments, such as the embodiments shown in FIG. 1 and FIG. 3, a switch 290 is configured as a component of the mobile imaging device 400, such as a home button of a smart phone type mobile imaging device 400. In some embodiments, the switch 290 is configured to implement, fire, or execute a method (e.g., method 1000 of FIG. 10, method 1300 of FIG. 13, etc.) or non-transitory computer readable storage medium including one or more programs of the imaging device 100. In some embodiments, the switch 290 is remotely activated, such as from a second mobile imaging device 400-2. The remote activation can be achieved through a sensor, a plurality of sensors, an electronic communication, or a wireless transmission. Thus, a user can remotely operate the imaging device 100 from a distance, which reduces a risk of harm to the user when emitting UV-C irradiation from the mobile imaging device. In some embodiments, such as the embodiment shown in FIG. 3, the switch 290 a physical mechanism disposed on an external surface of the housing 300. In various embodiments, the switch 290 can be configured as various ON/OFF mechanism such as a knob, a dial, a slide, and the like. In some embodiments, the switch 290 is a power supply switch of the imaging device 100, such that the switch 290 allows for a control of power to the plurality of light source sets 110 through the mobile imaging device 400. In some embodiments, a plurality of switches 290 can exists. Furthermore, use of the switch 290 allows for the distance between the imaging device 100 and the mobile imaging device 400 to increase to such distances, that the imaging device 100 can be mechanically coupled to a vehicle (e.g., a remote-controlled vehicle, a telescopic pole) and/or wirelessly communicate with the mobile imaging device 400, to allow remote control of the imaging device 100 through the switch 290 of the mobile imaging device 400.

Accordingly, a user interface according to an exemplary embodiment of the present disclosure achieves the advantages of allowing a user to optimize and customize firing the plurality of light source sets 110 of the imaging device 100. Furthermore, the user interface allows for the user to view a region of interest through a display of the mobile imaging device 400 when firing the plurality of light source sets 110, which is particularly important when emitting UV-C irradiation from the plurality of light source sets 110. In this way, the user can safely view the region of interest from the display of the mobile imaging device 400 without directly viewing the region of interest.

A control module 622 allows for a control of the imaging device 100 through the mobile imaging device 400. Specifically, the control module 622 facilitates determining and/or evaluating one or more conditions 624 of the control module 622 in order to allow for a firing (e.g., block 1004 and/or block 1006 of FIG. 10, block 1304 and/or block 1306 of FIG. 13, etc.) of the plurality of light source sets 110, such as allowing for an initial firing or a continuous firing of the plurality of light source sets 110. Furthermore, in some embodiments, each condition 624, or a subset of conditions 624, includes at least one corresponding specification, which provides a requirement of the boundary condition 624 in order for the boundary condition 624 to be deemed satisfied by the control module 622. For instance, in some embodiments, the control module 622 is in communication with the one or more sensors of the mobile imaging device 400 (e.g., accelerometer 417, gyroscope, etc.), and evaluates one or more measurements obtained from the one or more sensors in order to determine if a respective boundary condition 624 is satisfied by the one or more measurements. Said otherwise, the respective boundary condition 624 provides a quantifiable, objective requirement for allowing for the initial firing or the continuous firing of the plurality of light source sets 110, which improves safety for an end-user. For instance, in some embodiments, these one or more measurements include a corresponding value for the at least one corresponding specification of the condition 624. In this way, the one or more conditions 624 of the control module 622 provides a safety mechanism when the firing of the plurality of light source sets 110 can harm a user, such as when the user is exposed to UV-C irradiation from the plurality of light source sets 110. Additionally, in some embodiments, the condition 624 specification provides the requirements for satisfying the corresponding condition 624, such as a function to determine positional tolerance of movement of the mobile imaging device 400 when firing the plurality of light source sets 110. However, the present disclosure is not limited thereto. Furthermore, in some embodiments, the control module 622 provides a safety mechanism by ensuring that the region of interest has a sufficient exposure to UV-C irradiation emitted by the plurality of light source sets 110, such as providing dynamically updated conditions 624 that vary in accordance with one or more changes in position of the mobile imaging device 400. For instance, in some embodiments, the conditions 624 include one or more boundary conditions (e.g., a first plurality of conditions 624-1) having corresponding boundary condition specifications, which ensure the safety of the user before and/or during the firing of the plurality of light source sets 110, and/or one or more firing conditions (e.g., a second plurality of conditions 624-2), which further ensure the safety of the user when firing the plurality of light source sets 110 and/or provide parameters for firing the plurality of light source sets 110 outside of the boundary conditions 624. However, the present disclosure is not limited thereto. Additionally, in some embodiments, the one or more boundary conditions 624 provide one or more predetermined characteristics or settings (e.g., boundary conditions 624 for one or more predetermined regions of interest), and/or the one or more firing conditions 624 ensure sufficient sterilization of the region of interest when firing the plurality of light source sets 110 to irradiate the region of interest with UV-C light. In this way, in some embodiments, the boundary conditions 624 provide a traditional safety mechanism that allows for firing of the plurality of light source sets 110 and/or oversight conditions required to firing the plurality of light source sets 110, whereas the firing conditions 624 provide a negative control mechanism when the plurality of light source sets 110 emit light and/or ensure that the region of interest is exposed to light from the plurality of light source sets 110. However, the present disclosure is not limited thereto. In some embodiments, one or more conditions 624 is defined by the user, such as a first condition 624-1 restricting firing of the plurality of light source sets to a predetermined GPS region. In some embodiments, the one or more conditions 624 include a predetermined condition 624, such as a second condition 624-2 discontinuing power to the plurality of light source sets 110 in accordance with a determination that a change in Y-axis position of the mobile imaging device 400 is satisfied when firing the plurality of light source sets 110. Furthermore, in some embodiments, one or more conditions 624 is associated with a measurement from a corresponding sensor of the mobile imaging device 400 for a corresponding value of a respective condition 624, such that the one or more conditions 624 dynamically change based on the measurement from the corresponding sensor. By way of example, in some embodiments, a third condition 624-3 is associated with an evaluation of light obtained through an objective lens 210 of the mobile imaging device 400, such as to ensure the ROI is sufficiently illuminated by the plurality of light source sets 110. In some embodiments, one or more conditions 624 is associated with a measurement from a corresponding sensor of the mobile imaging device 400 for a corresponding value of a respective condition 624, such that the one or more conditions 624 dynamically change based on the measurement from the corresponding sensor but not the boundary condition specification, allowing for a static boundary condition specification, or a boundary condition specification that is first determined by the mobile imaging device 400 (e.g., acquired at block 1004 of FIG. 10) and held constant by the mobile imaging device 400 (e.g., evaluated at block 1006 of FIG. 10, firing of block 1304 of FIG. 13, determining of block 1306 of FIG. 13, etc.). However, the present disclosure is not limited thereto.

A non-limiting example of some a corresponding boundary specification of a condition 624 includes a threshold orientation tolerance of the mobile imaging device that discontinues power to the plurality of light source sets 110 when a first orientation of the mobile imaging device 400 satisfies the threshold orientation tolerance of 5° difference from an initial position of the mobile imaging device 400, 10° difference from an initial position of the mobile imaging device 400, 15° difference from an initial position of the mobile imaging device 400, 20° difference from an initial position of the mobile imaging device 400, 25° difference from an initial position of the mobile imaging device 400, or a combination thereof. Another non-liming example of the corresponding boundary specification of the condition includes a threshold distance between the mobile imaging device 400 and the region of interest that discontinues power to the plurality of light source sets 110 when a first distance satisfies the threshold distance of about 1 cm, about 3 cm, about 5 cm, about 10 cm, about 15 cm, about 20 cm, about 25 cm, about 30 cm, about 35 cm, about 50 cm, about 75 cm, about 100 cm, about 1,000 cm, about 2,000 cm, or a combination thereof. As yet another non-limiting example, in some embodiments, the corresponding boundary specification of the condition includes a threshold coverage area of light provided by the plurality of light source sets 110, a threshold dosage of light provided by the plurality of light source sets 110, and the like.

In some embodiments, the control module 622 stores one or more workflows including one or more predetermined conditions 624 for utilizing the mobile imaging device 400. For instance, in some embodiments, a first workflow is associated with a first subset of conditions 624 and a second workflow is associated with a second subset of conditions 624. If each subset of conditions 624 is associated with a unique region of interest, then either a first mobile imaging device 400-1 conducts the first workflow and the second workflow to sterilize both corresponding unique regions of interest, or the first mobile imaging device 400-1 conducts the first workflow and a second mobile imaging device 400-2 conducts the second workflow. In some embodiments, progress about a workflow (e.g., progress about conducting method 1000 of FIG. 10, method 1300 of FIG. 13, etc.) is further stored in the control module 622. However, the present disclosure is not limited thereto.

A workflow module 626 facilitates storing and generating one or more workflows. Each respective workflow defines parameters for firing the plurality of light source sets 110 (e.g., method 1000 of FIG. 10, method 1300 of FIG. 13, etc.), such as a respective plurality of conditions 624 associated with the firing of the plurality of light source sets 110. Specifically, the workflow module 626 includes a workflow store 628 that retains information related each workflow, such as each condition 624 utilized in the firing of the plurality of light source sets 110, each region of interest targeted in the firing of the plurality of light source sets 110, each image captured during a sequence for firing the plurality of light source sets 110, and the like. By way of example, if a user firing a first plurality of light source sets 110-1 of UV-B light in the plurality of light source sets 110 at a first region of interest identified as doorknob, and the firing is conducted based on a first plurality of conditions (e.g., a first condition 624-1 based on an exposure time, a second condition 624-2 based on a rotational movement of the mobile imaging device 400), a first workflow is retained by the workflow storage 626 that describes the firing the first plurality of light source sets 110-1 of UV-B light at the first region of interest identified as doorknob, and the firing is conducted based on a first plurality of conditions. In this way, the mobile imaging device 400 can repeat the first workflow, for instance, in accordance with a determination that a firing of the plurality of light source sets 110 did not satisfy a threshold sterilization of the first region of interest. Furthermore, in some embodiments, the mobile imaging device 400 communicates a retained workflow to a second mobile imaging device 400-2 or a server, allowing the retained workflow to be reiterated and/or evaluated outside of the mobile imaging device 400 computing environment. However, the present disclosure is not there. In some embodiments, a respective workflow retained by the workflow storage further includes information related to a location of a corresponding firing of the plurality of light source sets 110 (e.g., GPS coordinates of the corresponding firing, position data of the mobile imaging device 400, etc.), a time of the corresponding firing of the plurality of light source sets (e.g., date and/or time of the corresponding firing), and the like.

A workflow generator 630 facilitates generating one or more workflows for using in firing the plurality of light source sets 110 at a region of interest. For instance, in some embodiments, the workflow generator 630 evaluates a respective firing of the plurality of light source sets 110 (e.g., a respective instance of method 1000 of FIG. 10, a respective instance of method 1300 of FIG. 13, etc.), and generates a corresponding workflow based on the respective firing of the plurality of light source sets 110. In some embodiments, the workflow generator 630 receives data relating to one or more workflows of the workflow storage 626, and generates a first workflow based on the one or more workflows received from the workflow storage 626. In this way, the workflow generator 628 can produce novel workflows for firing the plurality of light source sets 110 based on previous instances of the firing of the plurality of light source sets 110. In some embodiments, the workflow generator 628 includes one or more evaluation models, which provide a unique evaluation of an input workflow. From this, the workflow generator 628 can utilize an evaluation model for generating a workflow that can verify and/or improve a previously generated workflow.

In some embodiments, the workflow generator 630 includes a decision tree evaluation model, a neural network evaluation model, a support vector machine (SVM) evaluation model, a Naïve Bayes evaluation model, a pattern-matching evaluation model, a Bayesian evaluation model, a rule based evaluation model, or a combination thereof. However, the present disclosure is not limited thereto. Furthermore, in some embodiments, the decision tree evaluation model, the neural network evaluation model, the SVM evaluation model, the Naïve Bayes evaluation model, the pattern-matching evaluation model, the Bayesian evaluation model, the rule based evaluation model, or the combination thereof is utilized in determining a characteristic (e.g., an identify, a material property) of a region of interest.

Additionally, in some embodiments, the workflow generator 630 facilitates determining if a corresponding value for one or more condition 624 of a first firing of the plurality of light source sets (e.g., block 1304 of FIG. 13) satisfies a corresponding condition specification based upon a plurality of measurements associated with a region of interest acquired from one or more sensors of the mobile imaging device 400. By way of example, in some embodiments, in accordance with a determination that the corresponding value for the one or more condition 624 of the first firing of the plurality of light source sets 110 does not satisfy the corresponding condition specification, the workflow generator products a workflow for a second firing of the plurality of light source sets that ensures the satisfy the corresponding condition specification. In this way, if a first firing of the plurality of light source sets 110 does not adequately satisfy one or more conditions 624, a second workflow is generated by the workflow generator 630 to ensure adequately satisfy the one or more conditions 624. In some embodiments, the second workflow includes one or more instructions, or notes, for the user to ensure satisfy the one or more conditions 624. For instance, in some embodiments, the second workflow displayed a note instructing the user to illuminate a first portion of the region of interest that did not satisfy the one or more conditions 624, or illuminates the first portion of the region of interest with a first light source set 110-1 to visible indicate the first portion of the region of interest. However, the present disclosure is not limited thereto. As such, this workflow generator requires a computer to be used because such considerations cannot be mentally solved. In other words, given an input to the computational model to collectively consider each respective result to generate a workflow, the computational model output needs to be determined using a computer rather than mentally in such embodiments.

Figure 10:
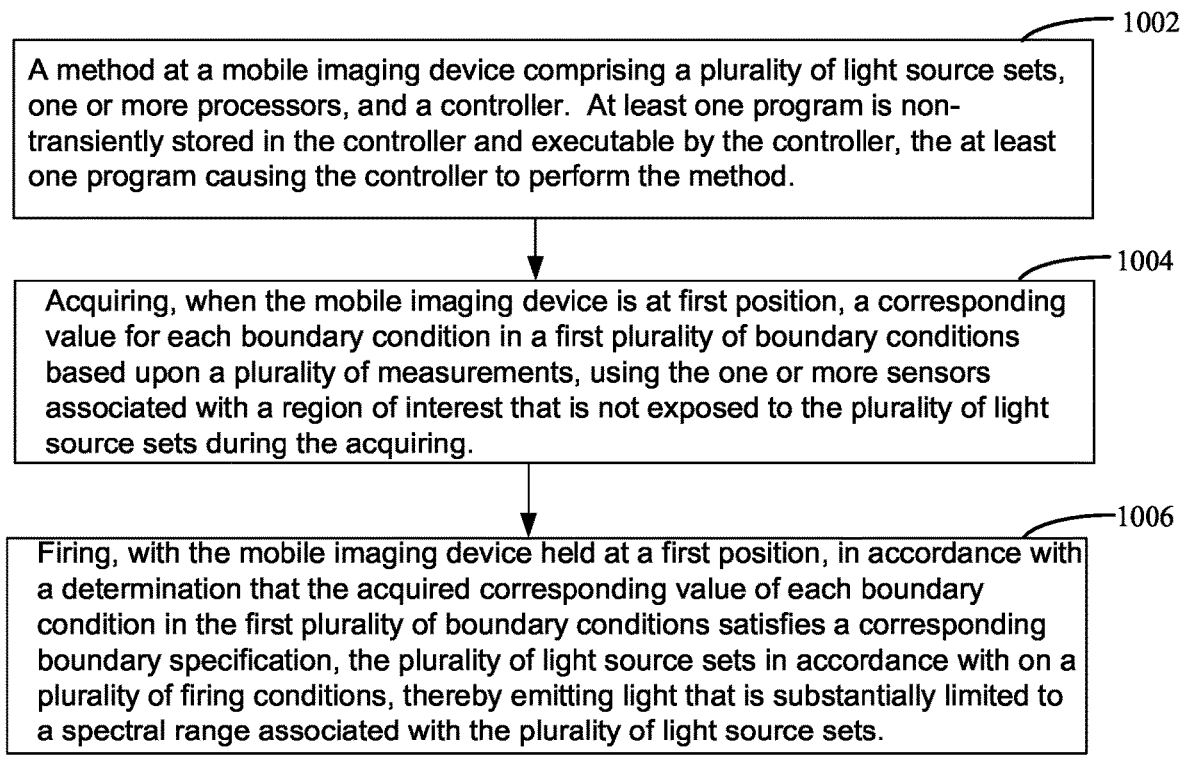
FIG. 10 illustrates a first flow chart of methods for utilizing a mobile imaging device using a device in accordance with an embodiment of the present disclosure.

In some embodiments, meta data is associated with captured multimedia (e.g., images and/or video of a region of interest) and/or a firing of the plurality of light source sets 110, such as a device identifier (e.g., identifying the mobile imaging device 400 within a group of mobile imaging devices 400 that fired a respective plurality of light source sets 110), which may include an arbitrary identifier, a MAC address, a device serial number, etc.), temporal meta data (e.g., date and time of a corresponding acquisition of conditions 624, date and time of a corresponding firing, such as block 1006 of FIG. 10, of the plurality of light source sets 110), location data (e.g., GPS coordinates of the location at which a plurality of light source sets 110 was fired, a position of the mobile imaging device 400, etc.), a firing frequency (e.g., a first frequency at which a stream of images is captured by the mobile imaging device 400, a second frequency at which the plurality of light sources sets 110 emit light, etc.), device configuration settings (e.g., image resolution captured multimedia items, frequency ranges that the pixilated detector of the mobile imaging device 400 is configured to detect, one or more boundary conditions 624 and/or one or more firing conditions 624 of the mobile imaging device 400, one or more determinations of satisfying the one or more conditions 624, one or more objects associated with the region of interest, etc.), and/or other camera data, data associated with the firing of plurality of light source sets 110 data, environmental factors associated with the firing of the plurality of light source sets 110. And data associated with the region of interest and/or one or more objects within the region of interest.

Accordingly, U.S. Pub. No.: 2017/0323472, entitled "METHODS AND SYSTEMS FOR SURFACE INFORMATICS BASED DETECTION WITH MACHINE-TO-MACHINE NETWORKS AND SMART PHONES," U.S. application Ser. No. 15/521,871, entitled "TEMPORAL PROCESSES FOR AGGREGATING MULTI DIMENSIONAL DATA FROM DISCRETE AND DISTRIBUTED COLLECTORS TO PROVIDE ENHANCED SPACE-TIME PERSPECTIVE," U.S. application Ser. No. 15/522, 175, entitled "METHODS AND SYSTEMS FOR REMOTE SENSING WITH DRONES AND MOUNTED SENSOR DEVICES," U.S. application Ser. No. 15/532,578, entitled "SWARM APPROACH TO CONSOLIDATING AND ENHANCING SMARTPHONE TARGET IMAGERY BY VIRTUALLY LINKING SMARTPHONE CAMERA COLLECTORS ACROSS SPACE AND TIME USING MACHINE-TO MACHINE NETWORKS," U.S. application Ser. No. 15/867,653, entitled "SYSTEMS AND METHODS FOR SPECTRAL IMAGING WITH A TRANSMITTER USING A PLURALITY OF LIGHT SOURCES," and U.S. application Ser. No. 16/780,755, entitled "SYSTEMS AND METHODS FOR SPECTRAL IMAGING WITH COMPENSATION FUNCTIONS," are each hereby incorporated by reference in their entirety.

It should be appreciated that the mobile imaging device 400 is only one example of a portable multifunction device, and that the mobile imaging device 400 optionally has more or fewer components than shown in FIG. 2, optionally combines two or more components, or optionally has a different configuration or arrangement of the components.

Figure 4:
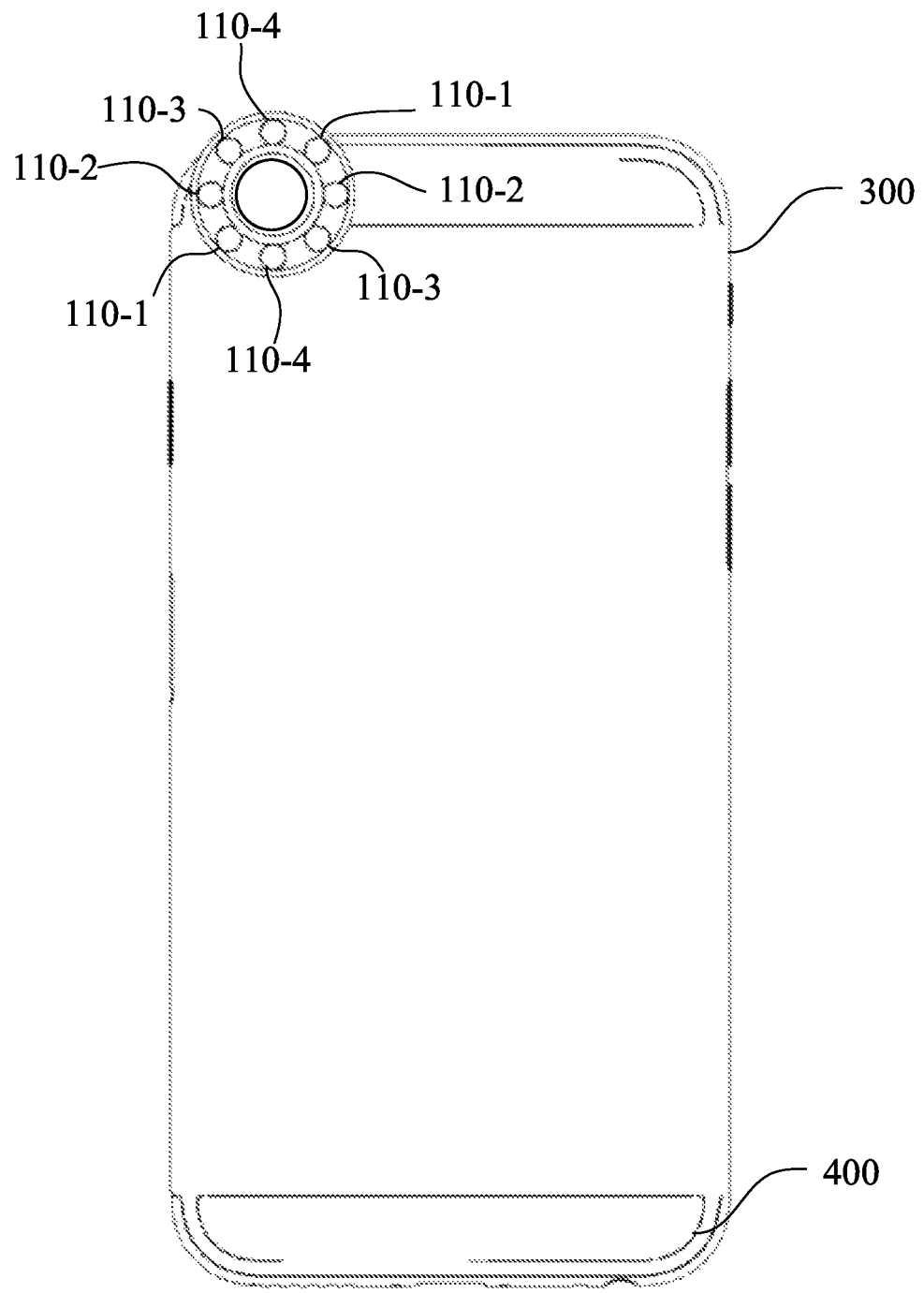
FIG. 4 is a front schematic view of a mobile imaging device according to another exemplary embodiment of the present disclosure.
Figure 5:
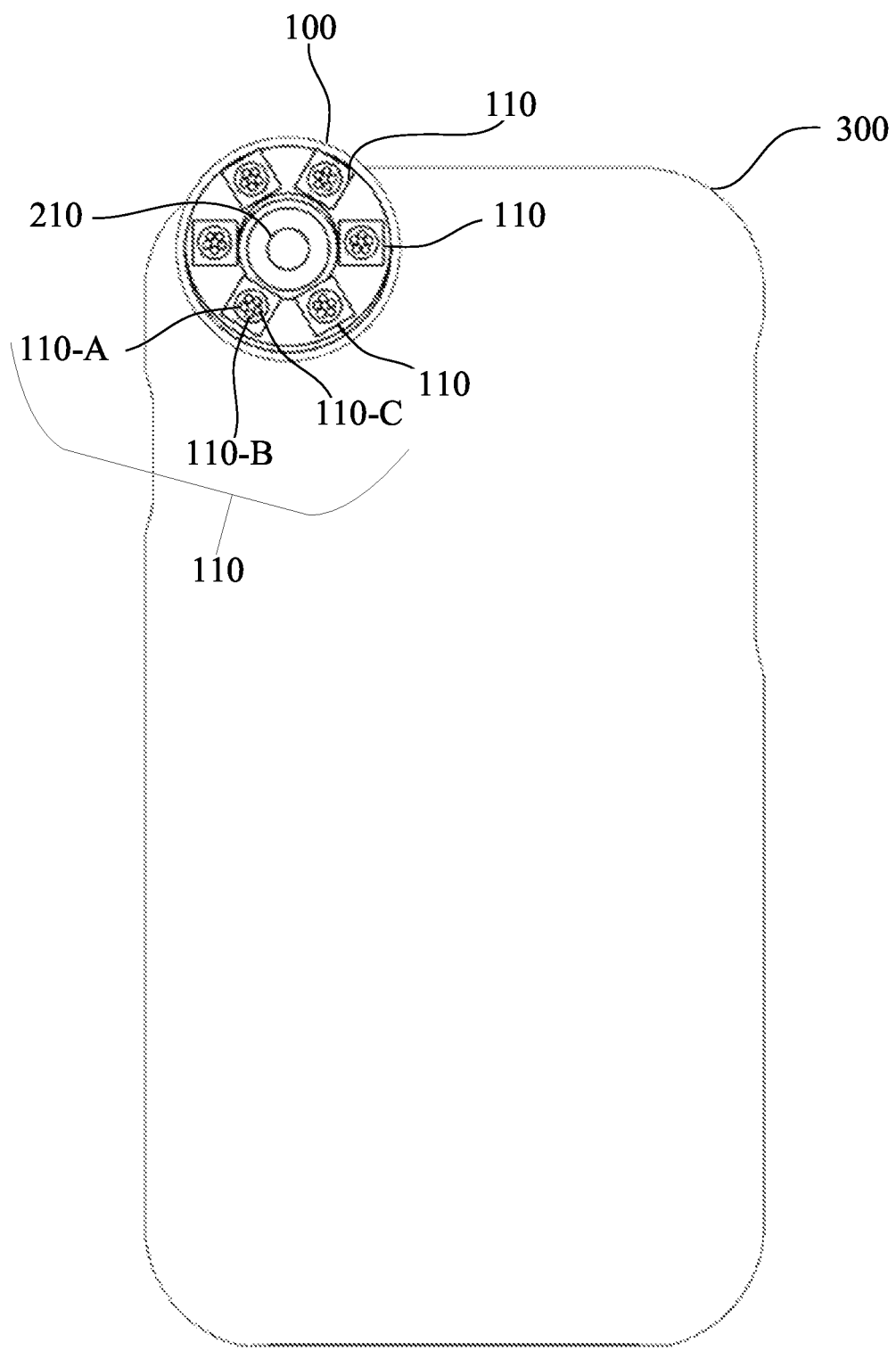
FIG. 5 is a front schematic view of a mobile imaging device according to yet another exemplary embodiment of the present disclosure.

FIG. 3, FIG. 4, and FIG. 5 collectively depict views of the mobile imaging device 400, the imaging device 100, and the housing 300 according to various embodiments of the present disclosure.

Referring to FIG. 3, the imaging device 100 includes an objective lens 210. The objective lens 210 is disposed within the housing 300. However, the present disclosure is not limited thereto. In some embodiments, the objective is flush with a surface of the housing 300, such that an upper end portion of the objective lens in in plane with an upper end portion of the housing 300. Thus, the objective lens 210 does not substantially extend past the upper end portion of the housing 300. However, the present disclosure is not limited thereto. For instance, in some embodiments, the objective lens 210 is recessed from the surface of the housing 300 and/or protrudes from the surface of the housing 300. Furthermore, in some embodiments, one or more optical mechanisms are coupled with the objective lens 210, such as one or more filters and/or a collimator (e.g., collimator and/or collar 1200 of FIG. 12), which reduces stray light. However, the present disclosure is not limited thereto. For instance, in some embodiments, the objective lens 210 is formed as a part of the mobile imaging device 400 (e.g., integrally formed with the mobile imaging device 400). In this way, the housing 300 and the imaging device 100 can communicate with the objective lens 210 of mobile-imaging device 400 without pre-configuration with the mobile imaging device 400.

As illustrated in FIG. 3, a plurality of light source sets 110 is attached or integrated into the housing 300. Each respective light source set (e.g., a first light source set 110-A, a second light source set 110-B, a third light source set 110-C, etc.) in the plurality of light source sets 110 includes a plurality of lights. In some embodiments, each plurality of lights is uniformly radially distributed about the objective lens 210. However, the present disclosure is not limited thereto. For instance, in some embodiments, the plurality of light sets 110 is distributed in an array about the objective lens 210. For instance, in other embodiments, each respective light source set (110-A, 110-B, 110-C) in the plurality of light source sets 110 can form a concentric circle about the objective lens 210. However, the present disclosure is not limited thereto. In such embodiments, there can exist k light source sets (110-A, 110-B, 110-C, 110-$i$, ..., 110-$k$) in the plurality of light source sets 110 forming a maximum of k concentric circles about the objective lens 210, where k is a maximum number of light source sets in the plurality of light source sets 110. In various embodiments, the plurality of lights source sets 110 can form a plurality of arc segments about the objective lens 210. The arc segments can be uniform. However, the present disclosure is not limited there to so long as the plurality of light source sets are uniformly distributed about the objective lens 210 in such embodiments.

In some embodiments, the plurality of light source sets 110 is distributed in a radial array about the objective lens 210, such as one or more concentric ellipses about the objective lens. In some embodiments, the radial array is a spiral, such as an Archimedean spiral that has a constant distance of separation between light source sets.

Figure 8A:
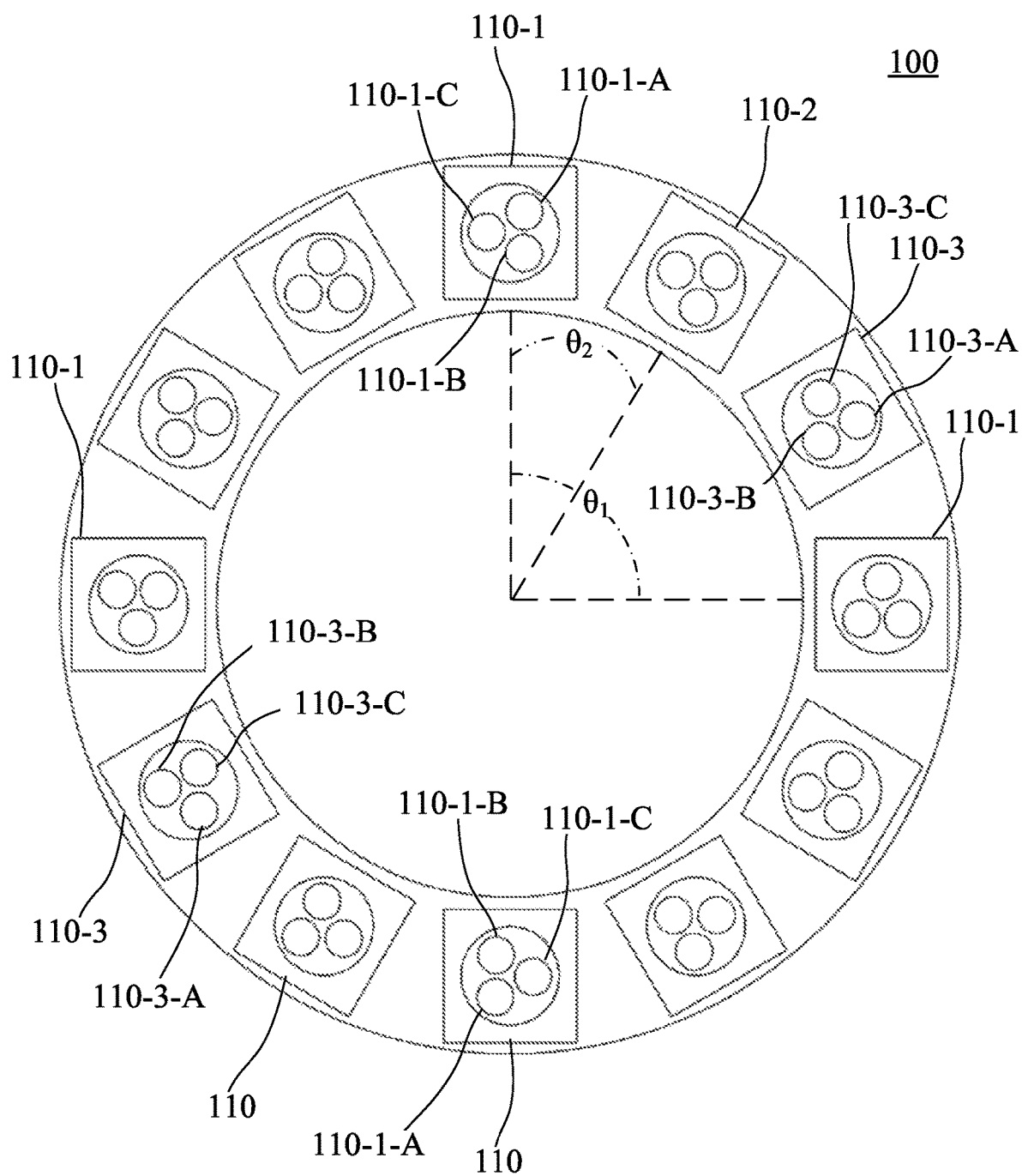
FIG. 8A, FIG. 8B, FIG. 8C, and FIG. 8D illustrate an enlarged schematic view of a plurality of light source sets according to an exemplary embodiment of the present disclosure.
Figure 8D:
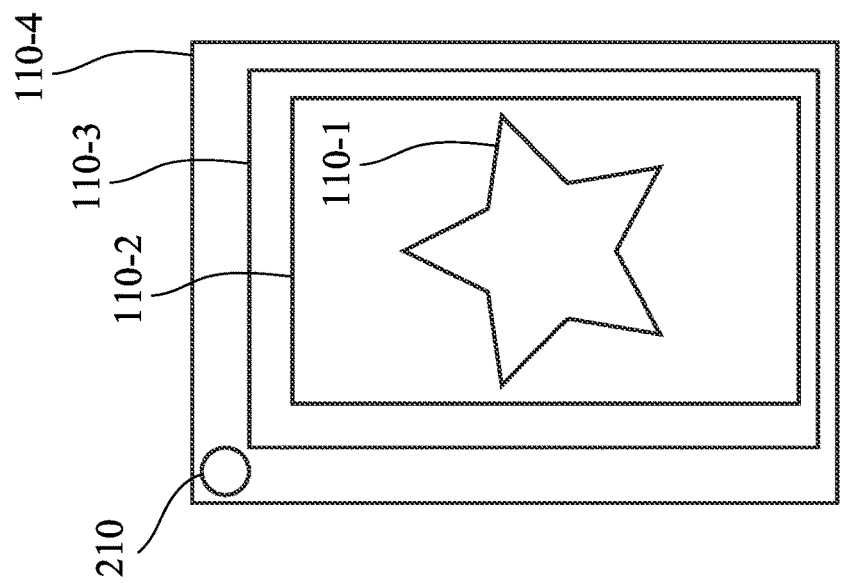
Figure 8C:
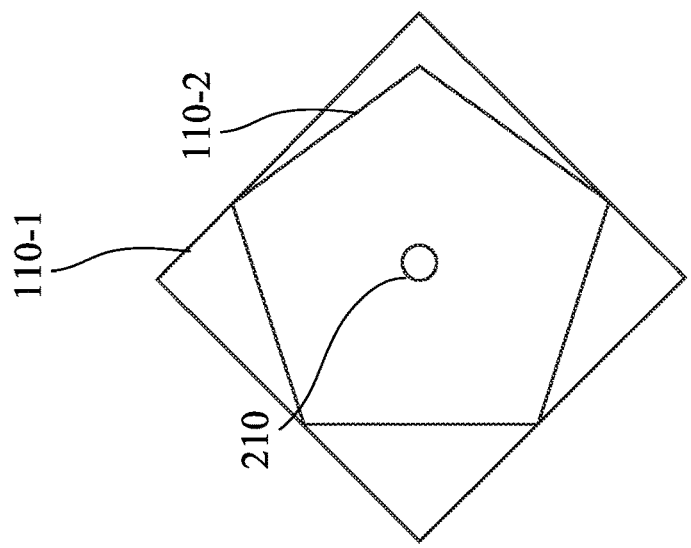
Figure 8B:
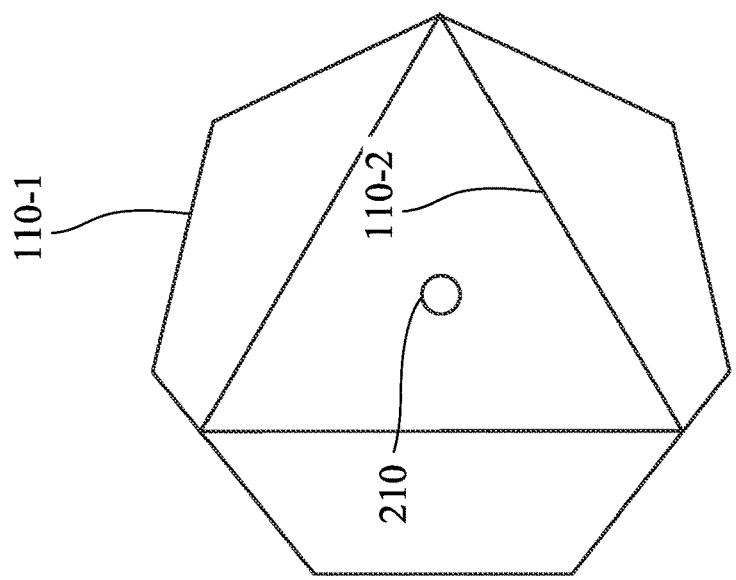
Figure 9:
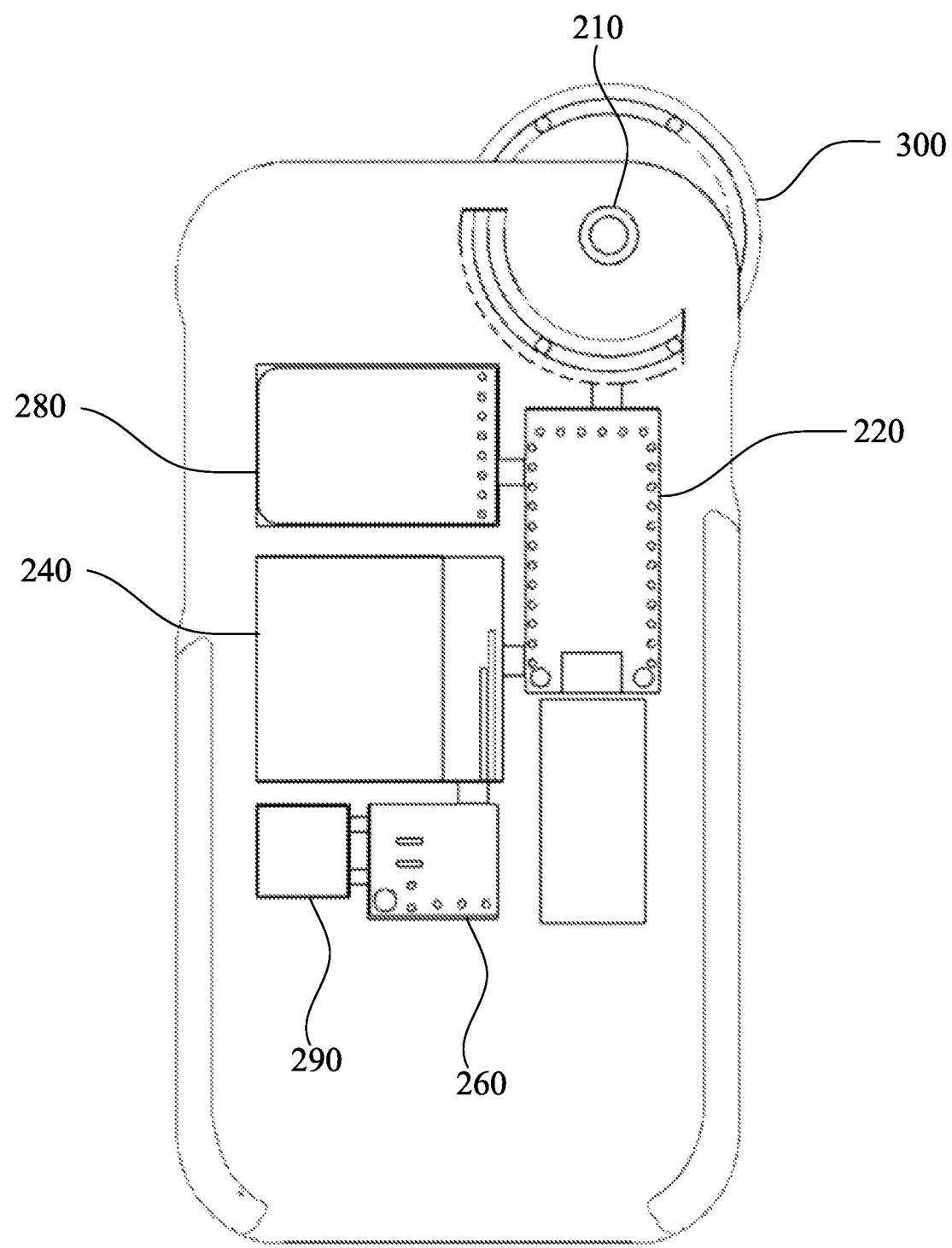
FIG. 9 is a rear schematic view of a housing of a mobile imaging device according to an exemplary embodiment of the present disclosure.

Furthermore, referring briefly to FIGS. 8A through 8D, in some embodiments, the array of the plurality of light source sets 110 is an array of two or more sets of light source sets 110. In FIGS. 8B through 8D, a light source set in a set of light source sets 110 is disposed at a respective vertex in the polygon, a point along an edge of the polygon, or within an area of the polygon. In some embodiments, the array of the plurality of light source sets is an array of two or more polygons, such as an array of two or more regular polygons including a first array of two or more concentric triangles, a second array of two or more concentric quadrilaterals, a third array of two or more concentric pentagons, a fourth array of two or more concentric hexagons, a fifth array of two or more concentric heptagons, or a combination thereof. As a non-limiting example, FIG. 8B illustrates the plurality of light source sets 110 distributed about the objective lens 210 in an array that includes a first set of light sources 110-1 in a heptagon and a second set of light sources in a triangle. In some embodiments, the array of the plurality of light source sets 110 is an array of two or more irregular polygons. Furthermore, in some embodiments, the array of the plurality of light source sets 110 is an array of at least one regular polygon and at least one irregular polygon.

In some embodiments, the objective lens 210 is a component of the mobile imaging device 400. However, the present disclosure is not limited thereto. For instance, in some embodiments, the objective lens 210 is a stand-alone device such as an auxiliary web camera in communication with the mobile imaging device 400. In various embodiments, the objective lens 210 is selected from the group consisting of a 3D binocular, a fiber optic, a fisheye lens, a macro lens, a microscopic lens, a normal lens, and a telephoto lens.

The type of objective lens 210 and spacing of the plurality of light source sets 110 varies greatly depending on application. For instance, an imaging device 100 utilized for small region of interest applications can have a region of interest ranging from 1 cm$^2$ to 10 cm$^2$ and a plurality of lights 110 disposed with a diameter ranging in between 0.5 cm to 10 cm. An imaging device 100 utilized for large regions of interest applications can have a region of interest ranging from 1 m$^2$ to hundreds of thousands of m$^2$ and a plurality of lights 110 disposed with a diameter ranging in between 0.5 cm to 10 cm. In such large region of interest applications, in some embodiments, a user combines a plurality of imaging devices 100 into an array of imaging devices 100 (e.g., an array including a first imaging device 100-1, a second imaging device 100-2, . . . , an i$^{th}$ imaging device 100-i, etc.). In such an embodiment, the plurality of imaging devices 100 form a plurality of light source sets 110, thus accomplishing the same objectives of a single imaging device 100 of the present disclosure yet on a larger scale. Naturally, embodiments in between such micro and macroscopic regions of interest exist are within the scope of the present disclosure. In some embodiments, the region of interest is any closed form shape (e.g., circular, elliptical, polygon, rectangular, etc.). However, the present disclosure is not limited thereto.

Figure 6:
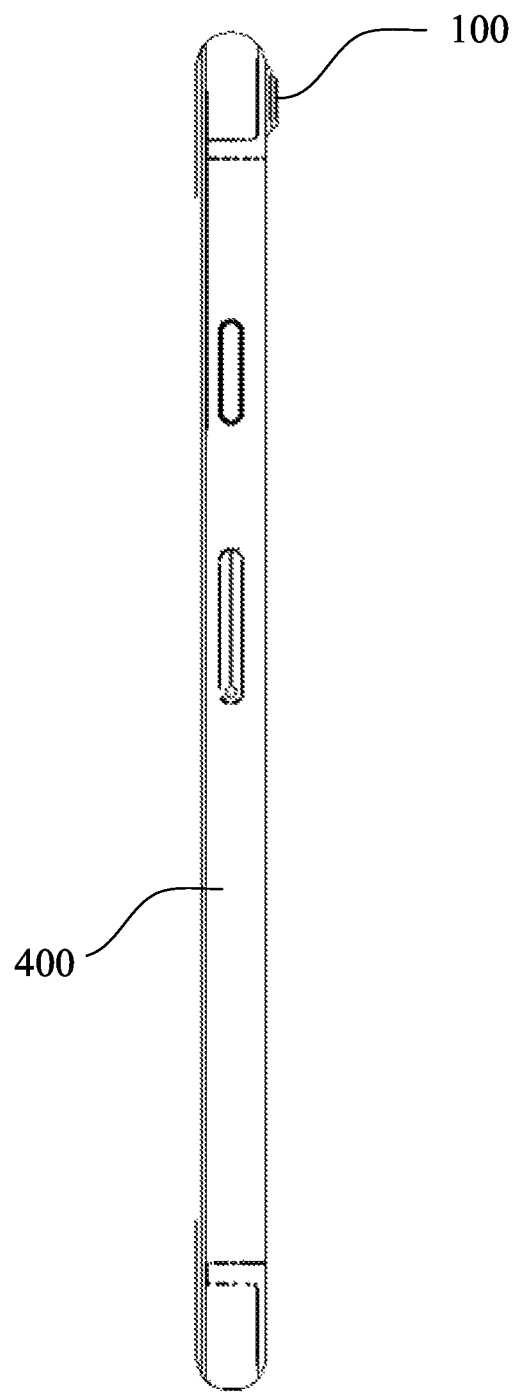
FIG. 6 is a side schematic view of a mobile imaging device according to a further exemplary embodiment of the present disclosure.

FIG. 6 depicts an embodiment of the present disclosure where an imaging device 100 is integrated with a mobile imaging device 400. In some embodiments, the plurality of light source sets 110, and thus the imaging device 100, is flush with a surface of the mobile imaging device 100. The term "flush," as used herein, is defined as a surface of a first component and a same respective surface of a second component to have a distance or level separating the first component and the second component to be 0.0 cm, within a tolerance of 50 μm, within a tolerance of 0.1 mm, within a tolerance of 0.1 cm, or within a tolerance of 0.25 cm. In some embodiments, the same respective surface of the second component is coplanar to the surface of the first component. An imaging device 100 considered to be flush with a mobile imaging device 400 can be either internally disposed within the mobile imaging device 400 or integrated with the mobile imaging device 400.

Referring to FIG. 4, in some embodiments, each light source set (110-1, 110-2, 110-3, 110-4) in the plurality of light source sets 110 contains a single light source. In the present embodiment, each single light source has a predetermined spectral range or wavelength. As such, in some embodiments, each light source set (110-1, 110-2, 110-3, 110-4) in the plurality of light source sets 110 emits a unique spectral range or wavelength associated with a corresponding predetermined spectral range. By way of example, a light source set 110-1 emits a first spectral range or wavelength, a light source 110-2 emits a second spectral range or wavelength, a light source 110-3 emits a third spectral range or wavelength, and a light source 110-4 emits a fourth spectral range or wavelength. As another non-limiting example, the first light source set 110-1 can emit UV-C light, the second light source set 110-2 can emit red light, the third light source set 110-3 can emit blue light, and the fourth light source set 110-4 can emit green light. However, the present invention is not limited thereto. In some embodiments, each light source set 110 is characterized by (e.g., emits) a predetermined spectral range or wavelength. In some embodiments, each light source set 110 is characterized by a different spectral range or wavelength that does not overlap with the spectral range or wavelength of any of the other light source set 110. For instance, in some embodiments, a first light source set 110-1 of the mobile imaging device 400 is characterized by a first spectral range of UV-C light (e.g., 255 nm to 270 nm), and a second light source set 110-2 of the mobile imaging device 400 is characterized by a first wavelength outside of the first spectral range (e.g., a blue wavelength of 470 nm). However, the present disclosure is not limited thereto. In some embodiments, each light source set 110 is characterized by a different spectral range that does not overlap with the spectral range of any of the other light source set 110 (e.g., a first light source set 110-1 characterized by UV-C light, a second light source set 110-2 characterized by UV-B light, a third light source set 110-3 characterized by visible light, etc.). In some embodiments, each light source set 110 is characterized by a different spectral range and the different spectral range of at least one light source set 110 that partially overlaps with the spectral range of another light source set 110. For instance, in some embodiments, a first source set 110 is characterized by a spectral range from x toy nm and a second first source set 110 is characterized by a spectral range from w to z nm, where w is between x and y.

In various embodiments, only a red spectral band light source set 110-1, a green light spectrum band light source set 110-2, a blue light spectrum band light source set 110-3, or a combination there exists in the plurality of light source sets 110. In such embodiments, the imaging device further includes a color detector. The color detector is configured to detect across the electromagnetic spectrum, specifically the visible light band in the present embodiment, and senses excitation light reflected from a region of interest. Red, green, and blue light wavelengths bands are distinct and can easily be differentiated from each other, thus, in some embodiments, the detector detect a multi-modal distribution of light. The multi-modal distribution can be analyzed to determine the specific of wavelengths or spectral bands of light detected by the color detector. Thus, a single image can be captured, analyzed, and processes to produce an image for analysis by the mobile imaging device 400. However, the present disclosure is not limited thereto. For instance, in some embodiments, the mobile imaging device 400 includes a light source set 110 characterized by UV-C irradiation.

In some embodiments, the plurality of light source sets 110 emits light from a predetermined spectral range. In this way, light emitted by the mobile imaging device 400 is limited to the predetermined spectral range. In some embodiments, the predetermined spectral range is from a first wavelength to a second wavelength (e.g., from 250 nm to 270 nm, from 260 nm to 270 nm). The first wavelength and the second wavelength are associated with a similar band of light or different bands of light. By way of example, in some embodiments, the first wavelength is a first region of the UV-C spectral range (e.g., from 260 nm to 264 nm) and the second wavelength is a second region of the UV-C spectral range different from the first region (e.g., from 265 nm to 270 nm), such that the first wavelength and the second wavelength are of the similar UV-C band. As another non-limiting the example, in some embodiments, the first wavelength is a first region of the UV-C spectral range (e.g., 260 nm-270 nm) and the second wavelength is a first region of the blue visible light range (e.g., 460 nm-470 nm), such that the first wavelength and the second wavelength are of dissimilar regions of the electromagnetic spectrum. In this way, the mobile imaging device 400 allows for the plurality of light source sets 110 to emit UV-C light when utilized by a user.

The embodiment shown in FIG. 4 depicts four light source sets (110-1, 110-2, 110-3, 110-4). However, the present disclosure is not limited thereto. In a further embodiment, the imaging device 100 includes k sets of light sources sets (110-A, 110-B, 110-i, . . . , 110-k) in the plurality of light source sets 110, where k is a positive integer greater than or equal to two. In some embodiments, the imaging device 100 includes two light source sets (e.g., first light source set 110-1, second light source set 110-2) in the plurality of light source sets 110. In another embodiment, the imaging device 100 includes four light source sets in the plurality of light source sets 110. In yet embodiment, the imaging device 100 include five light source sets in the plurality of light source sets, six light source sets in the plurality of light source sets, seven light source sets in the plurality of light source sets, eight light source sets in the plurality of light source sets, nine light source sets in the plurality of light source sets, ten light source sets in the plurality of light source sets, eleven light source sets in the plurality of light source sets, or twelve light source sets in the plurality of light source sets. In this way, the imaging device 100 can emit high intensity light through utilization of each light source in the plurality of light source sets 110. Moreover, when utilizing UV-C and by varying an exposure time, this high intensity light yields sufficient energy to inactivate one or more organisms within a region of interest, allowing for the mobile imaging device 400 to sterilize the region of interest from the one or more organisms.

In some embodiments, various light source sets 110 in the plurality of light source sets 110 share and/or overlap within a spectral range.

In some embodiments, the unique spectral range of each light source set 110 is defined by a given type of light source disposed in a respective light source set 110. However, the present disclosure is not limited thereto. For instance, in some embodiments, one or more filters is disposed interposing between a respective light source set 110 and the region of interest. In some embodiments, the plurality of light source sets 110 includes full spectrum light sources. In another embodiment, the plurality of light source sets 110 includes partial spectrum light sources including, but not limited to, halogen light sources, tungsten light sources, fluorescent light sources, and/or a combination thereof. In some embodiments, the plurality of light source sets 110 includes stable LEDs, tunable LEDs, or a combination thereof. In some embodiments, the plurality of light source sets 110 includes light sources that vary in wavelength with time or a predetermined function.

In some embodiments, the plurality of light source sets 110 include ultraviolet light source sets 110. By way of example, in some embodiments, the plurality of light source sets 110 include a first set of light source sets of UV LEDs, specifically UV-B LEDs and/or UV-C LEDs. In this way, the mobile imaging device 400 can emit UV-C irradiation through the plurality of light source sets 110 with sufficient energy to inactivate one or more active pathogens (e.g., kill cellular organism, inactivate a virus, etc.).

In some embodiments, the plurality of light source sets 110 includes a laser light source or a plurality of laser light sources. In some embodiments, a plurality of spot readings is simultaneously compiled for each laser light source in plurality of laser light sources. Laser light sources are particularly useful when a subject or region of interest is a solid color. However, the present disclosure is not limited thereto. In some embodiments, the plurality of light source sets 110 omit a laser light source; however, the mobile imaging device 400 considers light emitted by the plurality of light source sets 110 as if the laser light source were included in the plurality of light source sets 110. However, the present disclosure is not limited thereto.

Figure 12:
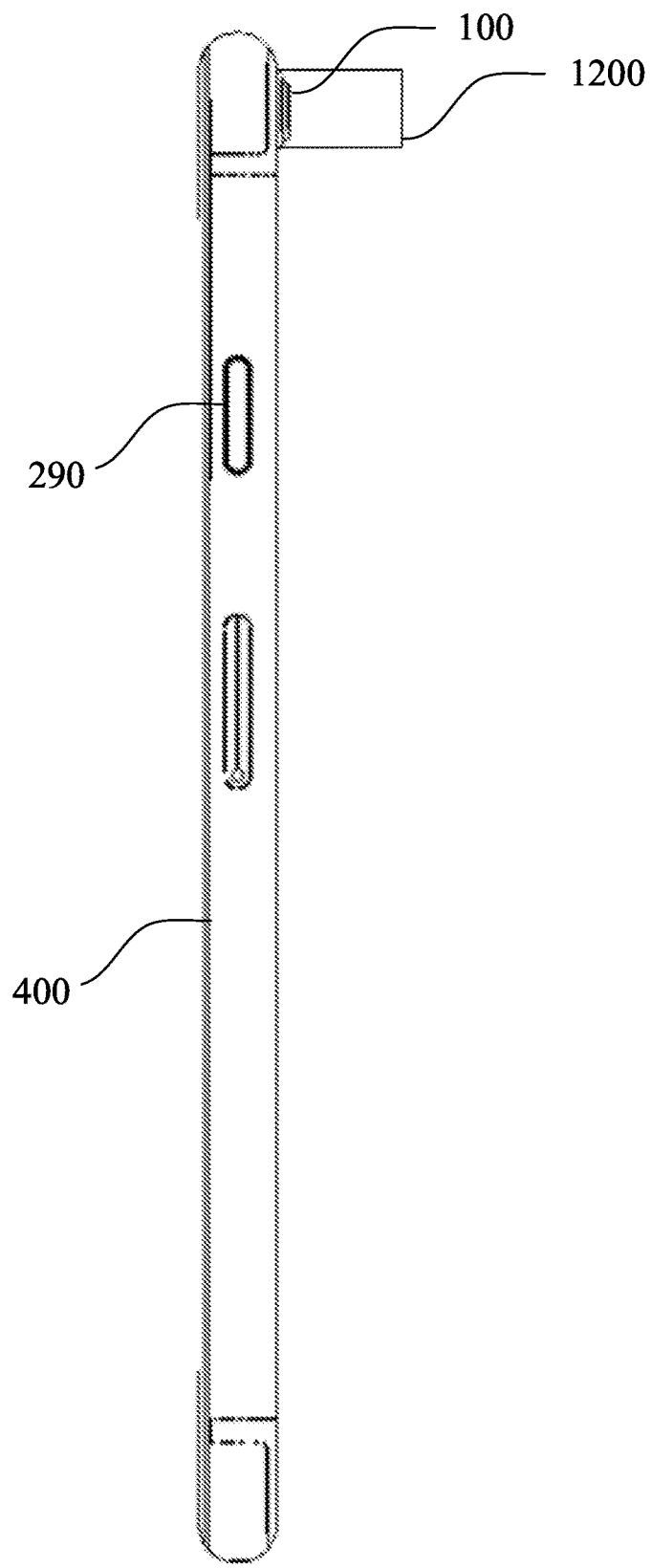
FIG. 12 is another side schematic view of a mobile imaging device according to yet a further exemplary embodiment of the present disclosure.

For instance, referring briefly to FIG. 12, in some embodiments, the mobile imaging device 400 includes a collimator or a collar (e.g., collar 1200 of FIG. 12) that surrounds a perimeter of the plurality of light source sets 110. The collar 1200 is configured to increase a fluence of light emitted by the plurality of light source sets 110 on a region of interest, while also, optionally, minimizing a risk of light emitted by the plurality of light source sets 110 from entering the peripheral vision of the user. Moreover, if a respective light source set 110 emits non-coherent light, the collar 1200 provides a physical mechanism to restrict a path of light of the non-coherent light, effectively increasing a fluence of light on the region of interest. For instance, some regulatory agencies, such as the United States Food and Drug Administration, consider UV-C light as non-coherent, and have prescribed performance standards for various light source sets. Miller et al., 2016, "Technical Electronic Product Radiation Safety Standards Committee Meeting: Non-Coherent Light Sources," U.S. Food and Drug Administration, print, which in hereby incorporated by reference in its entirety. In some embodiments, a length of the collar 1200 is in between 0.5 centimeters (cm) to 5 cm, from 0.5 cm to 4 cm, from 0.5 cm to 3.5 cm, from 1 cm to 3.5 cm, from 0.5 cm to 3 cm, from 1 cm to 4 cm, from 0.5 cm to 2.5 cm, from 1 cm to 2.5 cm, or a combination thereof. Furthermore, in some embodiments, the collar 1200 includes an aperture that provides a configurable opening at an upper end portion of the collar for light to transmit through from the plurality of light source sets 110. In some embodiments, the aperture of the collar 1200 is controlled by a user of the mobile imaging device 400, an application 500 of the mobile imaging device 400, or a combination thereof. Additionally, utilizing the collimator allows the mobile imaging device 400 to produce a collimated-beam from the plurality of light source sets 110-, which allows for providing an increased fluence of light on the region of interest.

In some embodiments, the first spectral range and the $k^{th}$ spectral range overlap but do not coexist. In other embodiments, the first spectral range and the $k^{th}$ spectral range overlap. In some embodiments, each spectral range in the plurality of spectral ranges is engineered for a specific predetermined wavelength or spectral range.

In some embodiments, emitted light has a radiant flux in between 5 milliwatts (mW) and 95 mW. In some embodiments, emitted light has a radiant flux in between 10 mW and 75 mw. In some embodiments, emitted light has a radiant flux in between 1 mW and 100 mW. In some embodiments, emitted light has a radiant flux in between 50 mW and 1000 mW. In some embodiments, emitted light has a radiant flux in between 0.01 mW and 100 mW. In some embodiments, emitted light has a radiant flux in of approximately 60 mW. By way of example, in some embodiments, the plurality of light source sets 110 includes five 60 mW 265 nm UV-C LED light sources. By utilizing UV-C irradiation with sufficient exposure times to sterilize a particular region of interest, the present disclosure allows for sterilization of pressure sensitive regions of interest, such as buttons on a keyboard, that otherwise would require a mechanical or chemical sterilization process.

In one implementation, the mobile imaging device 400 is configured to collect a set of images. The set of images is collected in order to determine particular characteristics of a region of interest, such as either at the mobile imaging device 400 or at a remote device. For instance, in some embodiments, each image is collected at a discrete spectral band and time period, and the set of images includes images collected at any two or more set of discrete spectral bands having central wavelengths. However, in the present disclosure is not limited thereto. In some embodiments, a first image is collected as a boundary condition 624, such as when a first light source set 110-1 in the plurality of light source sets 110-1 emits light, which has a wavelength in the visible region of the electromagnetic spectrum for 2 ms, and a second image is collected, such as when a second light source set 110-2 in the plurality of light source sets 110 emits light which has a wavelength of 265±5 nm for 9 ms. In this way, the mobile imaging device 400 can evaluate the second image against the first image to ensure safe firing of the plurality of light source sets 110. However, the present disclosure is not limited thereto. Furthermore, the above exposure times are not meant to significantly limit the present disclosure. For instance, in some embodiments each exposure time can vary by ±1 ms, ±2 ms, or ±5 ms. Additional details and information regarding the collection of one or more images will be described in more detail infra, particularly with respect to blocks 1004 and 1006 of FIG. 10.

Figure 7:
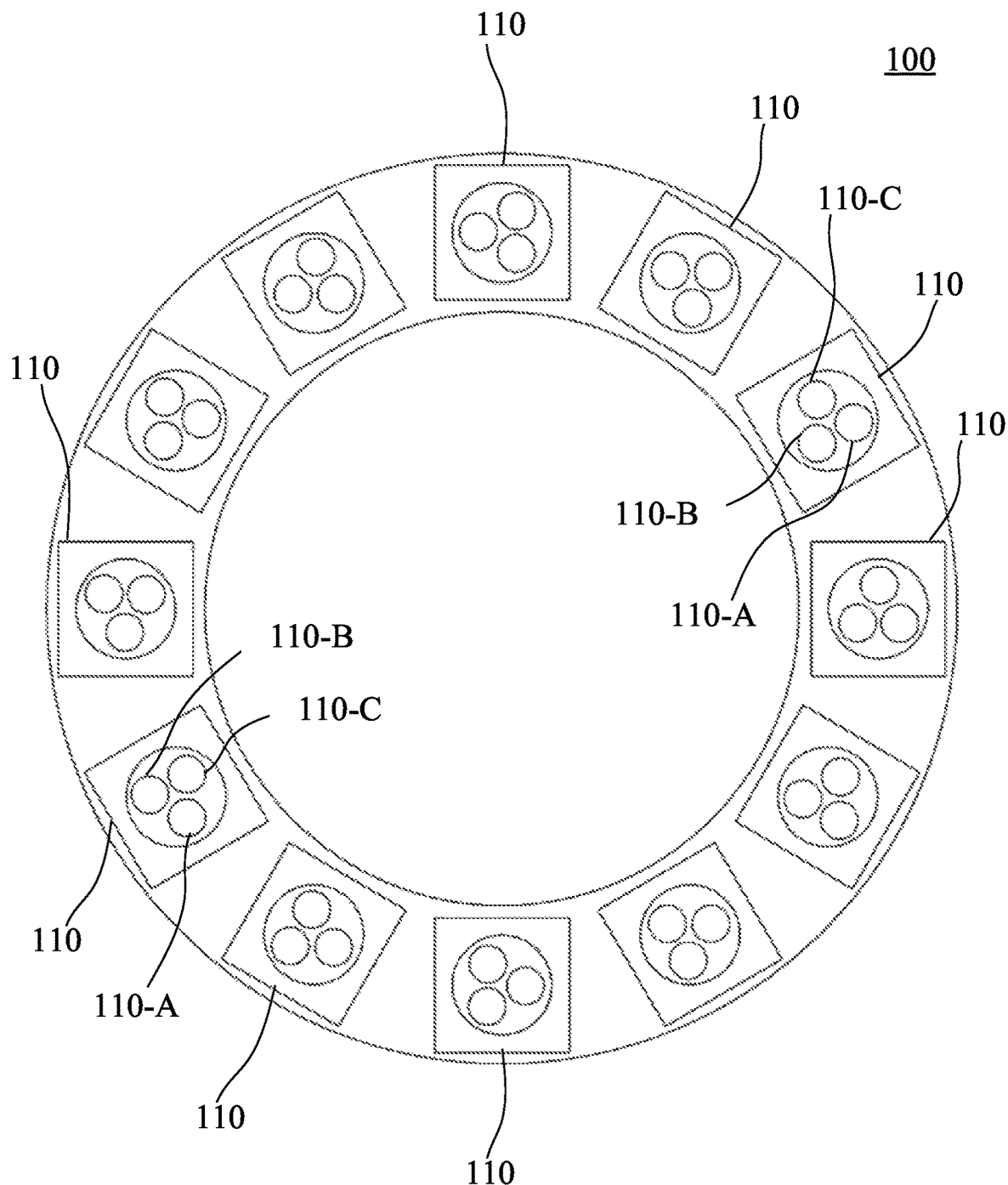
FIG. 7 is an enlarged schematic view of a plurality of light source sets according to an exemplary embodiment of the present disclosure.

In another embodiment, such as the embodiments shown in FIG. 5 and FIG. 7, the plurality of light source sets 110 includes a plurality of clusters includes the plurality of light source sets (110-A, 110-B, 110-C, . . . , 110-k). In such an embodiment, when each light source set (110-A, 110-B, 110-C, . . . , 110-k) is fired, the entire uniform radial distribution of lights can be illuminated. In other embodiments, uniformly distributed regions of the imaging device 100 can be illuminated.

Referring to FIGS. 8A through 8D, there can exist a plurality of light source sets (110-1, 110-2, 110-3) in the plurality of light source sets 110. Each light source set (110-1, 110-2, 110-3) in the plurality of light source sets 110 can consists of n light sources, where n is a positive integer. In the present embodiment, each light source set (110-1, 110-2, 110-3) includes a plurality of lights (110-$i$-A, 110-$i$-B, 110-$i$-C, 110-$i$-n). As such, each plurality of light sources of a respective light source set (110-1, 110-2, 110-3) in the plurality of light source sets 110, is disposed with $\theta_1$ degrees of separation to another plurality of light sources of the respective light source set (110-1, 110-2, 110-3) in the plurality of light source sets 110, where $$\theta_1 = \frac{360}{n}.$$

For example, in the present exemplary embodiment, each light source set (110-1, 110-2, 110-3) contains four plurality of light sources (e.g., there exist four iterations of 110-1), thus 90° of separation between each light source of a respective light source set.

Furthermore, in some embodiments, each plurality of lights (110-$i$-A, 110-$i$-B, 110-$i$-C, . . . , 110-$i$-n) of a respective light source set (110-1, 110-2, 110-3, . . . , 110-$i$, 110-$k$) is arranged with $\theta_2$ degrees of separation, where $$\theta_2 = \frac{360}{kn},$$

and k is a total number of light source sets, from an adjacent plurality of light sources of a different light source set in the plurality of light source sets. For example, in the present embodiment, there are three total light source sets (110-1, 110-2, 110-3) each of which contains four plurality of lights. Thus, each plurality of lights of the respective light source set in the plurality of light source sets is arranged with 30° of separation from an adjacent plurality of lights of a different light source set in the plurality of light source sets.

In some embodiments, lights sources of each respective light source set in the plurality of light source sets 110 are disposed at a same location. In such embodiments, a theoretical $\theta_2$ is zero.

The above spatial relationships ensure that a uniform light distribution pattern is emitted towards a region of interest while minimizing adverse luminance, such as UV-C irradiation that enters the peripheral vision of a user.

In some implementations, each respective light source of a respective light source set (e.g., 110-1-A, 110-2-A, 110-3-A) includes a unique discrete spectral range or wavelength. However, the present disclosure is not limited thereto.

In some embodiments, the battery 240, the power management circuit 260, and the communication interface 280, or a combination thereof is disposed within the housing 300. In other embodiments, the battery 240, the power management circuit 260, and the communication interface 280, or a combination thereof are disposed with the mobile imaging device 400. In some embodiments, the battery 240 is a rechargeable battery. For instance, in some embodiments, the battery 240 receives power from the power system 418 of the mobile imaging device 400, allowing for the mobile imaging device 400 to supplement power for components of the imaging device 100 (e.g., the plurality of light source sets 110).

In some embodiments, the communication interface 280 includes a wireless signal transmission element and instructions are sent in accordance with an imaging method (e.g., method 1000 of FIG. 10, method 1300 of FIG. 13, etc.) by the wireless signal transmission element. In various embodiments, wireless signal transmission element is selected from the group consisting of a Bluetooth transmission element, a ZigBee transmission element, and a Wi-Fi transmission element. In this way, the imaging device 100 can be controlled through the mobile imaging device 400, such that the mobile imaging device communicates one or more instructions (e.g., conditions 624) to the imaging device through the communications interface 280. Accordingly, the communications interface 280 allows a user to communicate instructions to one or many imaging devices 100 associated with the mobile imaging device 400.

In one implementation, the communication interface 280 includes a first communications interface 280. The imaging device 100 is coupled to the mobile imaging device 400, thereby bringing the first communications interface 280 in direct physical and electrical communication with a second communication interface of the mobile imaging device 400, thereby enabling instructions to be sent directly to the second communications interface from the first communications interface 280 in accordance with a method for firing the plurality of light source sets (e.g., method 1000 of FIG. 10, method 1300 of FIG. 13, etc.).

The imaging device 100 also includes a controller 220. The controller 220 includes at least one executable program non-transiently stored therein, and is configured to control at least the plurality of light source sets 110. In some embodiments, the controller 220 is a component of the mobile imaging device 400. However, the present disclosure is not limited thereto.

FIG. 10 collectively illustrates a flow chart of methods (e.g., method 1000) using a mobile imaging device in accordance with an embodiment of the present disclosure. In the flow chart, the preferred parts of the methods are shown in solid line boxes whereas optional variants of the methods, or optional equipment used by the methods, are shown in dashed line boxes.

Referring to block 1002 of FIG. 10, a method 1000 is performed at a mobile imaging device (e.g., mobile imaging device 400 of FIG. 2). The mobile imaging device 400 includes a plurality of light source sets (e.g., light source sets 110 of FIG. 4). Additionally, the mobile imaging device including one or more processors (e.g., CPU 402 of FIG. 2) and a controller (e.g., memory controller 468 of FIG. 2). At least one program (e.g., application 500 of FIG. 2) is non-transiently stored in the controller and executable by the controller. The at least one program causes the controller to perform the method 1000.

In some embodiments, the plurality of light source sets 110 includes at least two light source sets, at least three light source sets, at least five light source sets, at least six light source sets, at least eight light source sets, at least 10 light source sets, at least 15 light source sets, at least 20 light source sets, at least 25 light source sets, at least 50 light sources sets, or a combination thereof.

In some embodiments, the plurality of light source sets 110 includes a first light source set 110-1 that emits UV-C irradiation. In other embodiments, the plurality of lights source sets 110 only light sources in the UV-C range of the electromagnetic spectrum (e.g., 260 nm to 270 nm). In some embodiments, the plurality of light source sets 110 include a first light source 110-1 having from two UV-C LED light sources to fifteen UV-C LED light sources, from three UV-C LED light sources to ten UV-C LED light sources, from three UV-C LED light sources to eight UV-C LED light sources, from five UV-C LED light sources to ten UV-C LED light sources, or a combination thereof. In some embodiments, the plurality of light source sets 110 include the first UV-C light source sets 110-1 and a second light source set 110-2 associated with RGB LED light sources. However, the present disclosure is not limited thereto.

Block 1004. The method 1000 includes acquiring a corresponding value for each boundary condition in a first plurality of boundary conditions (e.g., conditions 624 of FIG. 2) when the mobile imaging device 400 is at a first position. As such, this acquiring the corresponding value for each boundary condition in the first plurality of boundary conditions requires a computer (e.g., the mobile imaging device 400) to be used because such acquisitions cannot be mentally solved. In other words, given an input to acquire the corresponding value, the output needs to be determined using a computer rather than mentally in such embodiments.

In some embodiments, the first plurality of boundary conditions includes at least 2 boundary conditions, at least 5 boundary conditions, at least 10 boundary conditions, at least 25 boundary conditions, at least 40 boundary conditions, at least 50 boundary conditions, at least 75 boundary conditions, at least 100 boundary conditions, at least 125 boundary conditions, at least 150 boundary conditions, at least 200 boundary conditions, at least 225 boundary conditions, at least 350 boundary conditions, at least 500 boundary condition, at least 750 boundary conditions, at least 2,000 boundary conditions, at least 5,000 boundary conditions, at least 10,000 boundary conditions, at least 75,000 boundary conditions, at least 200,000 boundary conditions, at least 500,000 boundary conditions, at least $1 \times 10^6$ boundary conditions, at least $5 \times 10^6$ boundary conditions, at least $1 \times 10^7$ boundary conditions, or a combination thereof. In some embodiments, the first plurality of boundary conditions is between 10,000 and $1 \times 10^7$, between 100,000 and $5 \times 10^6$, or between 500,000 and $1 \times 10^6$.

In some embodiments, the mobile imaging device 400 is held by hand of the user during the acquiring of the corresponding value, allowing for the mobile imaging device 400 to at least partially block the user, or a subject adjacent to the user, from directly viewing a portion of the region of interest, and, in some embodiments, light emitted by imaging device 100, particularly harmful UV-C irradiation. However, the present disclosure is not limited thereto. For instance, in alternative embodiments, the mobile imagining device 400 is mounted to a transport mechanism and/or a stationary mounting mechanism (e.g., tripod, etc.)

The corresponding value for each boundary condition 624 in the first plurality of boundary conditions 624 is acquired using the one or more sensors of the mobile imaging device 400, which collect a plurality of measurements associated with a region of interest (ROI) that is not exposed to the plurality of light source sets 110. However, the present disclosure is not limited thereto. In some embodiments, the plurality of measurements includes at least 2 measurements, at least 5 measurements, at least 10 measurements, at least 25 measurements, at least 40 measurements, at least 50 measurements, at least 75 measurements, at least 100 measurements, at least 125 measurements, at least 150 measurements, at least 200 measurements, at least 225 measurements, at least 350 measurements, at least 500 measurements, at least 750 measurements, at least 2,000 measurements, at least 5,000 measurements, at least 10,000 measurements, at least 75,000 measurements, at least 200,000 measurements, at least 500,000 measurements, at least $1 \times 10^6$ measurements, at least $5 \times 10^6$ measurements, at least $1 \times 10^7$ measurements, or a combination thereof. In some embodiments, the plurality of measurements is between 10,000 and $1 \times 10^7$, between 100,000 and $5 \times 10^6$, or between 500,000 and $1 \times 10^6$.

For instance, in some embodiments, the plurality of measurements is collected when the region of interest is exposed to visible light emitted from a respective light source set in the plurality of light source sets 110, such as when a flash of a camera of the mobile imaging device 400 or a remote light source is illuminating the region of interest. However, the present disclosure is not limited thereto. In some embodiments, the mobile imaging device 400 captures a first image in a set of images of the region of interest, and, based on an evaluation of the first image, acquires the first plurality of boundary conditions 624. By way of example, consider a first mobile imaging device 400-1 capturing a first image of a region of interest that is a keyboard. Based on an evaluation of the first image, either at the first mobile imaging device 400-1 or a remote device, one or more conditions 624 are acquired (e.g., retrieved from control module 622 of FIG. 2) for use when firing the plurality of light source sets at the region of the interest (e.g., block 1006 of FIG. 10). In some embodiments, the one or more condition 624 include a threshold dosage of light, a threshold coverage area of light, a threshold distance between the imaging device 400 and the region of interest, or a combination thereof. In some embodiments, the evaluation of the first image includes a determination that the region of interest includes, or optionally contains, one or more predetermined objects (e.g., in accordance with a determination that the first image includes a keyboard).

In some embodiments, the set of images includes at least 2 images, at least 5 images, at least 10 images, at least 25 images, at least 40 images, at least 50 images, at least 75 images, at least 100 images, at least 125 images, at least 150 images, at least 200 images, at least 225 images, at least 350 images, at least 500 boundary condition, at least 750 images, at least 2,000 images, at least 5,000 images, at least 10,000 images, at least 75,000 images or a combination thereof. In some embodiments, the set of images is between 1,000 and $1\times10^5$, between 10,000 and $5\times10^5$, or between 5,000 and $1\times10^6$.

In some embodiments, the one or more sensors includes a gyroscope, an accelerometer (e.g., accelerometer 417 of FIG. 2), or both. Accordingly, in some embodiments, the one or more sensors determinate a position of mobile imaging device at one or more points in time (e.g., a first position at a first point in time during block 1006 of FIG. 10, a second position at a second point of time during block 1006 of FIG. 10, etc.) as a respective measurement in the plurality of measurements. In some embodiments, the plurality of measurements include one or more translational position measurements, one or more rotational position measurements, or a combination thereof. For instance, in some embodiments, the plurality of measurements include a distance from a region of interest and/or an orientation of the mobile imaging device 400 and/or the imaging device 100 with respect to the region of the interest. In some embodiments, the plurality of measurements are obtained on a recurring basis, such as every 0.01 ms, every 0.1 ms, every 1 ms, every 10 ms, or every second. In some embodiments, the recurring basis is a non-periodic basis, such as an irregularly timed basis. By obtaining the plurality of measurements on a more rapid, recurring basis, a risk of harm to the user is greatly reduced, while also raising an accuracy of evaluating the plurality of measurements and/or the region of the interest.

In some embodiments, the first position of the mobile imaging device 400 is a predetermined position, and the acquired boundary conditions 624 are configured to ensure the device 400 is held at the first position. In this way, in some embodiments, a user configures the mobile imaging device 400 for firing the plurality light source sets 110 only in accordance with a determination that a respective mobile imaging device 400 is held at one or more predetermined positions. Accordingly, in some such embodiments, the user programs the one or more predetermined positions prior to operating the mobile imaging device 400 (e.g., by communication the one or more predetermined positions to the mobile imaging device 400 through communications network 106 of FIG. 1), which creates a workflow for firing the plurality of light source sets 110 at one or more regions of interest. However, the present disclosure is not limited thereto.

In some embodiments, the one or more sensors includes an objective lens (e.g., objective lens 210 of FIG. 3) and a two-dimensional pixelated detector in communication with the objective lens 210. Accordingly, the mobile imaging device 400 can receive optical information related to the region through the objective lens 210 and the two-dimensional pixelated detector. For instance, in some embodiments, the mobile imaging device 400 captures one or more images when the mobile imaging device 400 is held at the first position. The one or more images can then be used as baseline for evaluation of a condition 624 (e.g., as a negative control) when firing the plurality of light source sets 110 (e.g., block 1006 of FIG. 10), such as an evaluation to determine an identity of the region of interest and/or a subset of conditions 624. By way of example, in some embodiments, the mobile imaging device 400 captures a first image of the region of interest and evaluates the first image against one or more boundary conditions 624, thus ensuring that a future firing of the plurality of light source sets 110 is safe for the user (e.g., clear of an obstruction, such as a portion of the user's body) based on the evaluation of the first image. In some embodiments, this evaluation utilizes one or more feature recognition processes, such as a facial recognition process and/or body port recognition process. In some embodiments, this evaluation is based on a determination of one or more characteristics associated with the region of interest, such as a determined identity of the region of interest, one or more optical characteristics of the region of interest, and the like. In some embodiments, this evaluation includes requiring a presence of a first object in plurality of objects (e.g., presence of one or more corners of a keyboard) and/or absence of a second object in the plurality of objects (e.g., absence of a portion of a human user). However, the present disclosure is not limited thereto. In some embodiments, the first image is associated with a corresponding boundary specification of a respective condition 624.

In some embodiments, the one or more images when the mobile imaging device 400 is held at the first position is evaluated to determine one or more characteristics associated with a region of interest of the one or more images, such as a material of a surface of the region of interest (e.g., an evaluation of a reflectance of the surface of the region of interest), a presence of one or more objects in the region of interest (e.g., an evaluation of the first image determining if a portion of a human user is in the region of interest), and the like. In some embodiments, the one or more characteristics include an identity of the region of interest. In this way, the method 1000 allows for the mobile imaging device 400 to determine the identity of the region of interest, and, based on this identity, acquire values based on measurements from sensors for one or more boundary conditions 624 for use in firing the plurality of light source sets 110 and/or one or more boundary condition specifications for a respective boundary conditions 624 in the one or more boundary conditions 624.

In some embodiments, the one or more characteristics includes at least 2 characteristics, at least 5 characteristics, at least 10 characteristics, at least 25 characteristics, at least 40 characteristics, at least 50 characteristics, at least 75 characteristics, at least 100 characteristics, at least 125 characteristics, at least 150 characteristics, at least 200 characteristics, at least 225 characteristics, at least 350 characteristics, at least 500 boundary condition, at least 750 characteristics, at least 2,000 characteristics, at least 5,000 characteristics, at least 10,000 characteristics, at least 75,000 characteristics or a combination thereof. In some embodiments, the plurality of characteristics is between 1,000 and $1 \times 10^5$, between 10,000 and $5 \times 10^5$, or between 5,000 and $1 \times 10^6$.

Figure 11:
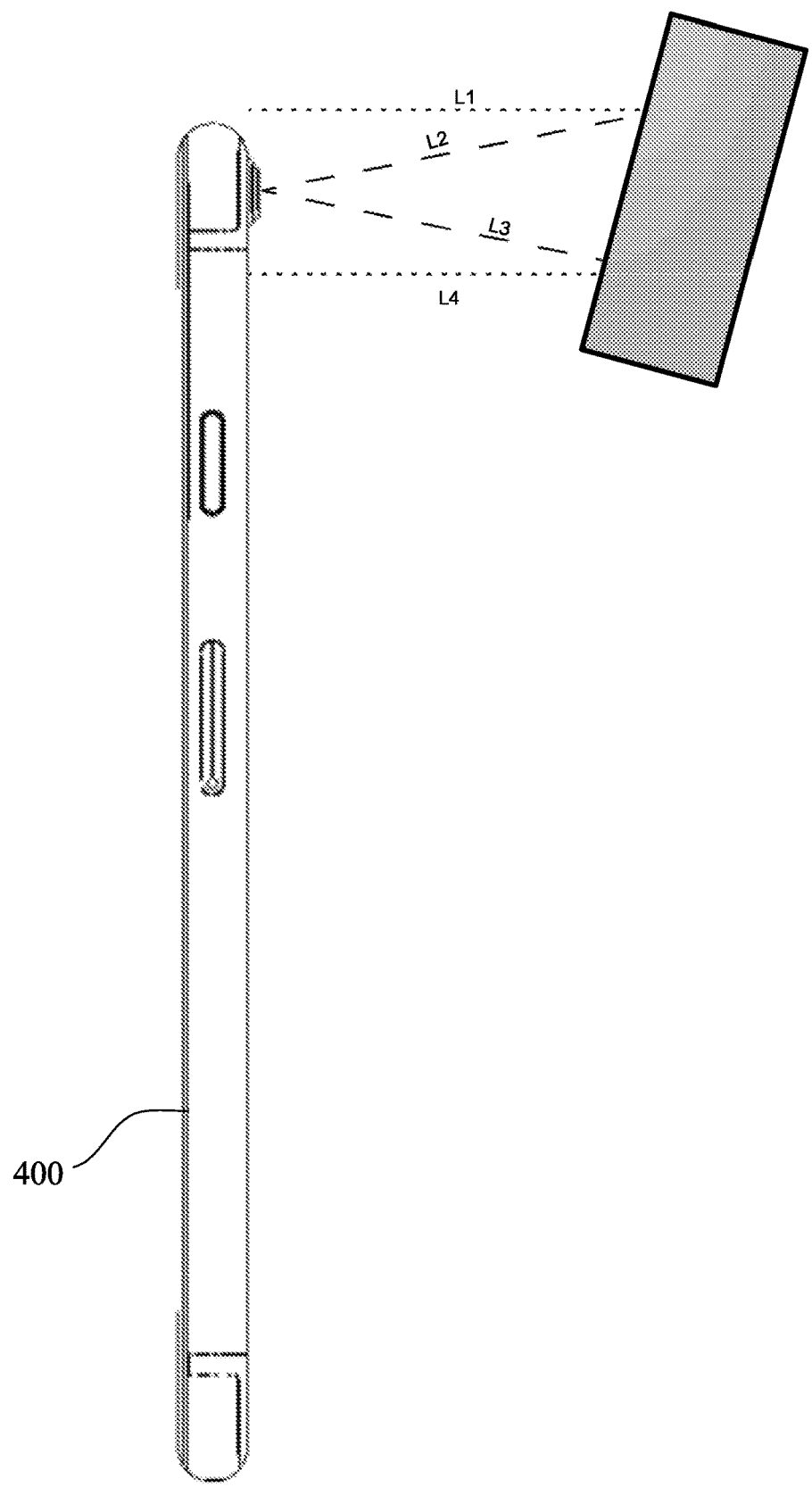
FIG. 11 is another side schematic view of a mobile imaging device according to a further exemplary embodiment of the present disclosure.

In some embodiments, the objective lens 210 is utilized to determine a corresponding value of a condition 624 having a boundary condition specification associated with a distance between the mobile imaging device 400 and the region of interest (e.g., L1, L2, L3, L4 or combination thereof of FIG. 11) and/or the imaging device 100 and the region of the interest. However, the present disclosure is not limited thereto. For instance, in some embodiments, a laser ranger finder mechanism of the mobile imaging device 400 facilitates the determination of the corresponding value of the condition 264 described supra. From this, the mobile imaging device 400 can determine an area effected by light from the plurality of light source sets 110 (e.g., triangular region formed by lines L2 and L3 with the gray shaded region of interest of FIG. 11, which, in some embodiments, provides a cone of irradiation from the mobile imaging device 400) as a corresponding value for a respective condition 624. For instance, in some embodiments, the mobile imaging device 400 determines an area (e.g., surface area) of the region of interest through the objective lens 210 as the corresponding value of the respective boundary condition 624 associated with the surface area of the region of interest, and the boundary condition specification provides the required thresholds to satisfy the respective boundary condition 624. However, the present disclosure is not limited thereto. Moreover, in some embodiments, the distance between the mobile imaging device 400 and the region of interest and/or the imaging device 100 and the region of the interest is utilized for a respective condition 624, such as a boundary condition 624. By way of example, in some embodiments, the distance between the mobile imaging device 400 and the region of interest and/or the imaging device 100 and the region of the interest is utilized as the corresponding value of the boundary condition 624 to determine an exposure time associated with the boundary condition specification of the boundary condition 624 when firing the plurality of light source sets 110. For instance, a shorter distance yields a shorter exposure time as compared to a longer distance in order to inactivate one or more organism of the region of the interest, such that the boundary condition specification provides a range of required exposure times to inactivate the one or more organisms and the mobile imaging device 400 acquires values from the one or more sensors associated with ensuring satisfying the boundary condition specification. However, the present disclosure is not limited thereto. With this exposure time, the mobile imaging device 400 can determine a fluence (e.g., $mw/cm^2$) and/or a dosage (e.g., integral of fluence with respect to time, milliJoules (mJ)/$cm^2$) for firing the plurality of light source sets 110. In some embodiments, a threshold exposure time is in a range of from 0.1 seconds to 1 second, from 0.5 seconds to 5 seconds, from 1 second to 10 seconds, from 5 seconds to 15 seconds, from 10 seconds to 60 seconds, from 30 seconds to 300 seconds, from 180 seconds to 6,000 seconds, or a combination thereof. In some embodiments, the dosage is approximately 5 $mJ/cm^2$, approximately 25 $mJ/cm^2$, approximately 50 $mJ/cm^2$, approximately 75 $mJ/cm^2$, approximately 100 $mJ/cm^2$, approximately 125 $mJ/cm^2$, or a combination thereof. However, the present disclosure is not limited thereto.

Block 1006. The method 1000 includes firing the plurality of light source sets 110 with the mobile imaging device 400 held at the first position based on a plurality of firing conditions (e.g., a second plurality of conditions 624-2 of FIG. 2). The firing of the mobile imaging device 400 is in accordance with a determination that the corresponding value of each boundary condition 624 in the first plurality of boundary conditions 624-1 satisfies the boundary condition specification. For instance, in accordance with a determination that the corresponding value which is an angel of incidence between the mobile imaging device 400 and the region of interest is within the boundary condition specification of a respective boundary condition 624. From this, the mobile imaging device 400 emits light that is substantially limited to a spectral range associated with the plurality of light source sets 110. Moreover, this emission of light is conditioned based on the satisfying on the first plurality of boundary conditions 624-1 and the plurality of firing conditions 624-2 through the corresponding values acquired by the one or more sensors of the mobile imaging device 400 that satisfy the corresponding boundary condition specifications. These condition 624 are configured to ensure that the mobile imaging device 400 fires the imaging device 100 to emit light from the plurality of light source sets 110 in accordance with a determination that the condition specifications 624 are satisfied from the corresponding value of the measurements obtained by the one or more sensors. In this way, a user of the mobile imaging device 400 is provided with supplemental, configurable control of the imaging device 100 through the conditions 624, while also providing safety and/or failsafe features for the firing of UV-C light from the plurality of light source sets 110. Furthermore, these conditions ensure that the firing of the plurality of light source sets 110 provides sufficient exposure of UV-C irradiation at the region of interest to satisfy a threshold level of sterilization (e.g., 3 log sterilization). As such, this firing the plurality of light source sets 110 in accordance with the determination that each condition in the first plurality of conditions satisfies the corresponding boundary condition specification requires a computer (e.g., the mobile imaging device 400) to be used because such determinations cannot be mentally solved. In other words, given an input to determine that each condition satisfies the corresponding boundary condition specification, the output needs to be determined using a computer rather than mentally in such embodiments.

In some embodiments, the plurality of firing conditions includes at least 2 firing conditions, at least 5 firing conditions, at least 10 firing conditions, at least 25 firing conditions, at least 40 firing conditions, at least 50 firing conditions, at least 75 firing conditions, at least 100 firing conditions, at least 125 firing conditions, at least 150 firing conditions, at least 200 firing conditions, at least 225 firing conditions, at least 350 firing conditions, at least 500 boundary condition, at least 750 firing conditions, at least 2,000 firing conditions, at least 5,000 firing conditions, at least 10,000 firing conditions, at least 75,000 firing conditions or a combination thereof. In some embodiments, the plurality of firing conditions is between 1,000 and $1 \times 10^5$, between 10,000 and $5 \times 10^5$, or between 5,000 and $1 \times 10^6$.

In some embodiments, the plurality of firing conditions 624 includes a resolution of an imaged captured though the objective lens 210. For instance, in some embodiments, a first condition 624-1 is associated with a threshold resolution, which ensures than an adequate resolution image is captured by the mobile imaging device 400. In this way, if an image captured by the objective lens 210 does not satisfying the resolution threshold, the firing of the plurality of light source sets 110 discontinues.

In some embodiments, the acquiring of the first plurality of boundary conditions 624-1 (e.g., block 1004) includes acquiring a first image through the objective lens 210. Moreover, the firing includes acquiring a second image through the objective lens 210. For instance, in some embodiments, the objective lens 210 of the mobile imaging device 400 is configured to face a user of the mobile imaging device 400, such that one or more images of the user is acquired at one or more steps of the firing of the plurality of light source sets (e.g., block 1004 and/or block 1006 of method 1000 of FIG. 10). For instance, in some embodiments, the mobile imaging device 400 evaluates (e.g., a Bayesian evaluation model) the second image to determine if a user is operating the mobile imaging device 400 and/or looking at the mobile imaging device 400. In some embodiments, the evaluation to determine if the user is operating the mobile imaging device 400 includes considering if the user as a portion of a second region of interest, such that a respective condition 624 requires a presence of a corresponding object (e.g., a face of a user) in the second region of interest if firing the plurality of light source sets 110. Additional details and information regarding an evaluation of an image can be found at Bauml et al., 2010, "Multi-pose Face Recognition for Person Retrieval in Camera Networks," IEEE International Conference on Advanced Video and Signal Based Surveillance, which is hereby incorporated by reference in its entirety.

In addition, the plurality of firing conditions 624 includes an evaluation of the second image based on the first image. For instance, in some embodiments, the evaluation of the second image is based on a comparison of a first aspect of the second image against a second aspect of the first image, such as a brightness of the ROI. However, the present disclosure is not limited thereto. For instance, in some embodiments, the second image is communicated to a remote device and/or stored at the mobile imaging device 400 for future consideration in a further firing of the plurality of light source sets 110.

In some embodiments, the first plurality of boundary conditions 624-1 includes a position tolerance of the mobile imaging device 400. The position tolerance of the mobile imaging device 400 allows for the mobile imaging device 400 to be held within a restricted range of movements, such as always held in a first orientation (e.g., always held downwards), restricting movement in a first axis (e.g., no positive Z-axis motion away from the region of interest), and the like. By way of example, in some embodiments, the position tolerance includes a boundary condition 624 allowing for a natural movement induced from being held by an unsteady human hand when firing the plurality of light source sets 110 (i.e., sway caused by the hand of the user). As another non-limiting example, the position tolerance includes a boundary condition 624 allowing for a greater movement of the mobile imaging device 400, such as movement within a predetermined area around the region of interest, such as three centimeters from an edge of the region. In this way, the mobile imaging device 400 can sanitize a first larger region of interest when the objective lens 210 and/or the plurality of light source sets 110 is restricted to a second smaller region of interest. However, the present disclosure is not limited thereto. In some embodiments, the position tolerance of the mobile imaging device 400 is based on the first position of the mobile imaging device.

Specifically, in some embodiments, the position tolerance boundary condition 624 of the mobile imaging device 400 includes one or more translational position tolerances of the mobile imaging device 400, such as a first tolerance for an allowance of translational movement of the mobile imaging device 400 in a X-axis when firing the plurality of light source sets 110, a second tolerance for an allowance of translational movement of the mobile imaging device 400 in a Y-axis when firing the plurality of light source sets 110, a third tolerance for an allowance of translational movement of the mobile imaging device 400 in a Z-axis when firing the plurality of light source sets 110, or a combination thereof. In some embodiments, the position tolerance boundary condition 624 includes one or more rotational position tolerances of the mobile imaging device 400, such as a fourth tolerance for an allowance of rotational movement of the mobile imaging device 400 about the X-axis when firing the plurality of light source sets 110, a fifth tolerance for an allowance of rotational movement of the mobile imaging device 400 about the Y-axis when firing the plurality of light source sets 110, a sixth tolerance for an allowance of rotational movement of the mobile imaging device 400 about the Z-axis when firing the plurality of light source sets 110, or a combination thereof. Accordingly, the position tolerance boundary condition 624 allows for an emission of UV-C light from the plurality of light source sets 110 only when the mobile imaging device 400 is kept within the above described tolerances. From this, the mobile imaging device 400 can discontinue emission of UV-C light from the plurality of light source sets 110 (e.g., power management 240) in accordance with the determination that the mobile imaging device 400 is held outside of the above-described position tolerance boundary condition 624. In some embodiments, the position of the mobile imaging device 400 is based on a relative position of an imaging device (e.g., imaging device 100 of FIG. 2) with respect to the mobile imaging device 400, such as if a distance between the mobile imaging device 400 and the imaging device 100 is large.

In some embodiments, the one or more translational position tolerances boundary conditions 624 includes a translational movement from the region of interest (e.g., the third tolerance for translational movement in the Z-axis) in a range from 0.1 inches to 100 inches, from 0.2 inches to 50 inches, from 0.5 inches to 50 inches, from 1 inch to 40 inches, from 1 inch to 25 inches, from 2 inches to 20 inches, from 2 inches to 15 inches, from 3 inches to 15 inches, from 4 inches to 15 inches, from 5 inches to 15 inches, from 5 inches to 10 inches, or a combination thereof. In this way, the translational position tolerance boundary condition 624 can be configured for a small tolerance (e.g., 0.25 inches) to restrict movement of the mobile imaging device 400, or configured to a large tolerance (e.g., 12 inches) to allow for a broad range of movement for an increased region of interest. Furthermore, in some embodiments, the one or more rotational position tolerance boundary conditions 624 includes a rotational movement from the region of interest (e.g., the fifth tolerance for rotational movement about the Y-axis) in a range of from 0 degrees to ±120 degrees, from 0 degrees to ±90 degrees, from ±5 degrees to ±120 degrees, from ±5 degrees to ±90 degrees, from ±5 degrees to ±70 degrees, from ±5 degrees to ±60 degrees, from ±5 degrees to ±45 degrees, from ±10 degrees to ±45 degrees, from ±10 degrees to ±20 degrees, or a combination thereof. However, the present disclosure is not limited thereto.

In some embodiments, the plurality of firing conditions 624 includes a second position of the mobile imaging device 400 based on the first position of the mobile imaging device 400. In some embodiments, the second position of the mobile imaging device 400 includes, or consists of, one or more rotational positions of the mobile imaging device 400, a vertical translational position of the mobile imaging device 400, or both, which is different from a corresponding axis of the first position of the mobile imaging device 400. In some embodiments, the first and second positions of the mobile imaging device are determined by one or more of the aforementioned sensors of the mobile imaging device 400. In this way, the user can be prevented from moving the mobile imaging device 400 when firing the plurality of light source sets 110 after one or more initial conditions 624 were satisfied for the firing of the plurality of light source sets 110. Furthermore, through this, the user can be directed towards one or more portions of a region of interest based on the aforementioned tolerances. For instance, in some embodiments, the mobile imaging device 400 fires the plurality of light source sets 110 in accordance with a determination that relative distance between a current location of the mobile imaging device 400 and a maxima of the tolerance positions is at a negative rate of change, such as when the mobile imaging device 400 is moving away from a restricted area. In this way, if a user does not expose a portion of the region of interest to the UV-C irrational emitted by the firing of the plurality of light source sets 110, the position tolerances can assist the user in ensuring that the position of the region of interest is exposed in a further firing of the plurality of light source sets 110.

In some embodiments, the spectral range of light emitted by the plurality of light source sets 110 is in between 250 nanometers (nm) and 270 nm, such that the imaging device 100 is capable of emitting UV-C irradiation. In some embodiments, the spectral range is in between 260 nm to 270 nm. In this way, the mobile imaging device 400 provides an emission of UV-C irradiation with sufficient energy to inactivate one or more active organisms of the region of interest or interposing between the region of interest and the imaging device 100. However, the present disclosure is not limited thereto.

In some embodiments, the firing of the plurality of light source sets 110 further includes, in accordance with a determination that a respective boundary condition 624 in the plurality of boundary conditions 624 or the plurality of firing conditions 624 is not satisfied, discontinuing powering to the plurality of light source sets 110. However, the present disclosure is not limited thereto. By way of example, in some embodiments, the mobile imaging device 400 communicates an instruction to the imaging device 100 (e.g., through network 606) to discontinues power to the plurality of light source sets 110, upon which the imaging device discontinues power through the power management 240. In other embodiments, the mobile imaging device 400 discontinues power of the plurality of light source sets 110 directly through the power system 418 of the mobile imaging device 100. However, the present disclosure is not limited thereto.

In some embodiments, the firing of the plurality of light source sets 110 further includes, in accordance with a determination that a respective boundary condition 624 in the plurality of boundary conditions 624 or the plurality of firing conditions 624 is not satisfied, firing a second plurality of light source sets 110-2 in the plurality of light sources sets 110 (e.g., within a spectral range outside of the UV-C spectral range of the first plurality of light source sets 110-1). In this way, the firing of the second plurality of light source sets 110-2 providing a visual indication that the respective boundary condition 624 in the plurality of boundary conditions 624 or the plurality of firing conditions 624 is not satisfied.

In some embodiments, the plurality of firing conditions 624 includes an exposure time for emitting light from the plurality of light source sets 110. In some embodiments, the exposure time is in between 0.5 seconds to 60 seconds, from 0.5 seconds to 30 seconds, from 1 second to 30 seconds, from 1 second to 25 seconds, from 2 seconds to 25 seconds, from 2 seconds to 20 seconds, from 5 seconds to 20 seconds, from 5 seconds to 15 seconds, from 3 seconds to 15 seconds, from 5 seconds to 10 seconds, from 3 seconds to 10 seconds, or a combination thereof. In some embodiments, the exposure time about or more than 3 seconds, about or more than 4 seconds, about or more than 5 seconds, about or more than 6 seconds, about or more than 7 seconds, about or more than 8 seconds, about or more than 10 seconds, about or more 15 seconds, about or more than 20 seconds, or a combination thereof. By modifying an exposure time of light emitted by the plurality of light source sets 110, the conditions 624 reduces a likelihood of harming a user of the mobile imaging device 400 when emitting UV-C irradiation through the plurality of light source sets 110. In some embodiments, the exposure time is determined based on one or more positions of the imaging device 100 and/or the mobile imaging device 400, including the first position of the mobile imaging device (e.g., first position of block 1004 of FIG. 10) and/or a second position of the imaging device (e.g., a second position of block 1006 of FIG. 10). For instance, in some embodiments, in accordance with a determination that a position of the mobile imaging device 400 changes (e.g., a distance between the plurality of light source sets 110 and the region of interests increases or distances, and angel of incidence of light at the region of interest, etc.), the firing of the plurality of light source sets 110 can concurrently, or in a future firing, change, to ensure sufficient sterilization of the region of interest.

In some embodiments, the region of interest includes one or more active organisms, such as on a surface of the region of interest. In some embodiments, the region of interest includes a surface of an object, such as a desk, and/or particles (e.g., airborne matter) interposing between the surface of the object and the plurality of light source sets 110. However, the present disclosure is not limited thereto. As described supra, in some embodiments, the region of interest is a three dimensional region of interest, such as a fluidic solution. In this way, the mobile imaging device 400 can utilize UV-C irradiation emitted from the plurality of light source sets 110 to inactivate one or more active organisms on various dimensions of regions of interests, when the mobile imaging device 400 is held by a user and one or more conditions 624 is satisfied. In some embodiments, the inactivation of the one or more organisms causes an inactivation threshold of organisms in the one or more organisms to become inactive. By way of example, in some embodiments, the inactivation threshold is greater than about 90% of the organisms become inactive (e.g., a 90% disinfection rate, D90 pathogen inactivation rate, 1 log in activation). In some embodiments, the inactivation threshold is in a range from about 90% to about 99.9%. However, the present disclosure is not limited thereto. For instance, in some embodiments, the inactivation threshold is in a range of from a first logarithmic base to a second logarithmic base (e.g., 1 log inactivation to 3 log inactivation). Furthermore, at an individual level, the mobile imaging device 400, by employing germicidal irradiation through emitting UV-C irradiation through the plurality of light source sets 110 of the imaging device 100, to commonly used, frequently touched regions of interest for direct, targeted interaction between the regions of interest and the UV-C irradiation.

In some embodiments, the one or more active organisms includes one or more viruses (e.g., a DNA virus such as P22 bacteriophage), one or more bacteria (e.g., *E. coli*, fungal spores, fungal cells/yeast, bacterial spores, vegetative bacteria, etc.), or both. However, the present disclosure is not limited thereto. In this way, the one or more active organisms is affected by UV-C light emitted by the mobile imaging device 400. In some embodiments, the firing of the plurality of light source sets 110 causes the one or more active organisms to become inactive. By causing the one or more active organisms of the region of interest to become inactive, the mobile imaging device 400 effectively exterminates, virally deactivates, etc. the one or more active organisms. From this, the region of interest (e.g., a surface of the region of interest, a volume of solution of the region of interest, etc.), or matter interposing between the region of interest and the mobile imaging device 400, becomes sanitized of the one or more active organisms. Additional details and information regarding the inactivation of one or more active organism and ultraviolet spectral band sources can be found at Wladyslaw Kowalski, 2010, "Ultraviolet Germicidal Irradiation Handbook: UVGI for Air and Surface Disinfection," Springer Science and Business Media, print, which is hereby incorporated by reference in its entirety.

In some embodiments, a third image is captured after the firing of the plurality of light source sets 110 is complete. The third image can then be evaluated, such as a comparison to the first image captured before the firing of the plurality of light source sets 110 and/or a second image captured during the firing of the plurality of light source sets 110. In this way, in some embodiments, the method 1000 can capture images at one or more periods of time and store these images for evaluation (e.g., a first period of time during block 1002 of FIG. 10, a second period of time during block 1004 of FIG. 10, and a third period of time during block 1006 of FIG. 10, etc.). For instance, in some embodiments, an image captured by the mobile imaging device 400 is stored for a reference (e.g., retained by workflow storage 628 of FIG. 2) against a future image capture at a first mobile imaging device 400-1.

In some embodiments, the mobile imaging device 400 includes a power supply (e.g., power system 418 of FIG. 2), that is configured for at least powering the mobile imaging device 400 and the plurality of light source sets 110. In this way, the present disclosure provides mobile imaging devices 400 that not only emit UV-C but also utilize one or more sensors and a controller to control the emission of UV-C light from the plurality of light source sets 110. From this, users can sterilize a region of interest safely through the mobile imaging devices 400 without requiring training or risking harm through the UV-C light. Moreover, the present disclosure also for one to configure one or more conditions 624, which dictate how a user conducts firing the plurality of light source sets 110, which provides a level of remote control over the mobile imaging device 400 and reduces a risk of harm for users of the mobile imaging device 400.

Light components within the plurality of light source sets 110 can differ from each other in terms of type, shape, size, light wavelength, light intensity, or the like. In some embodiments, an effectiveness of different light components (e.g., semiconductor dies) varies largely with luminous intensity differences of multiple orders of magnitude, which can be configured through the application 500 of the mobile imaging device 400. Those differences can to some degree be compensated by implementing multiple light components of the same spectral range to match the effectiveness of another, since lumens add up.

In some embodiments, the mobile imaging device 400 includes J light source sets 110 (i.e., each package includes J light components) for emitting light of K spectral ranges. J is a positive integer of three or greater, and K is a positive integer smaller than J. Each spectral range is different from any other spectral range in the K spectral ranges. For each respective $k^{th}$ spectral range in the K spectral ranges, the J light source sets 110 includes corresponding $j_k$ light source set or sets, wherein $j_k$ is a positive integer of one or greater, and $\Sigma_{k=1}^{K} j_k = J$. As such, at least for one specific spectral range in the K spectral ranges, there are multiple light components in each package that emit light of this specific spectral range.

In some embodiments, two or more light source sets 110 in the J light source sets 110 emit light that is substantially limited to a first spectral range, and one or more light source sets 110 in the J light source sets 110 emit light that is substantially limited to a second spectral range other than the first spectral range.

In some embodiments, one or more light source sets 110 in the J light source sets 110 emit light that is substantially limited to a third spectral range other than the first and second spectral ranges.

In some embodiments, a collective lighting intensity produced by the two or more light source sets 110 that emit light substantially limited to the first spectral range and a collective lighting intensity produced by the one or more light source sets 110 that emit light substantially limited to the second spectral range are substantially the same. For instance, in some embodiments, the collective lighting intensity produced by the four light source sets 110 including light components 110-B-1, 110-B-2, 110-B-3 and 110-B-4 of each package is substantially the same as the collective lighting intensity produced by the one light source set 110 including light component 110-A of each package.

In some embodiments, a collective lighting intensity produced by the two or more light source sets 110 that emit light substantially limited to the first spectral range, a collective lighting intensity produced by the one or more light source sets 110 that emit light substantially limited to the second spectral range, and a collective lighting intensity produced by the one or more light source sets 110 that emit light substantially limited to the third spectral range are substantially the same. For instance, in some embodiments, the collective lighting intensity produced by the two light source sets 110 including light components 110-1B-1 and 110-1B-2 of each package, the collective lighting intensity produced by the one light source sets including light component 110-1A of each package, and the collective lighting intensity produced by the one light source set 110 including light component 110-1C or 110-2A of each package are substantially the same.

In some embodiments, the light components are configured to maximize the spectral response in the desired spectral range or ranges of a region of interest. For instance, the specifications of the light components (e.g., spectral position and intensity) can be adjusted to maximize the spectral response in the desired spectral range or ranges.

A light component can emit near infrared light, visible light, ultraviolet light, or other light, and the emitted light can be of a narrow spectral band or a continuous spectral range. For instance, in some embodiments, the light components 110-1a, 110-1b and 110-1c emit UV-C light whereas light component 110-2a emits visible light of a continuous spectral range. Each of light components 110-1a, 110-1b and 110-1c emits UV-C light of a different narrow spectral band.

In some embodiments, the imaging device 100 includes light source sets emitting light that is substantially limited to 250±1 nm, 250±5 nm, 255±1 nm, 255±5 nm, 260±1 nm, 260±5 nm, 265±1 nm, 265±5 nm, 270±1, 270 nm±5, or a combination thereof. In this way, the mobile imaging device 400 provides a controlled emission from a UV-C region of the electromagnetic spectrum from a remote device (e.g., mobile imaging device 400) held by a user. However, the present disclosure is not limited thereto.

FIG. 13 collectively illustrates a flow chart of methods (e.g., method 1300) using a mobile imaging device in accordance with an embodiment of the present disclosure. In the flow chart, the preferred parts of the methods are shown in solid line boxes whereas optional variants of the methods, or optional equipment used by the methods, are shown in dashed line boxes.

Block 1302. Referring to block 1302 of FIG. 13, a method 1300 is performed at a mobile imaging device (e.g., mobile imaging device 400 of FIG. 2, mobile imaging device 400 of method 1000 of FIG. 10, etc.). The mobile imaging device 400 includes a plurality of light source sets (e.g., light source sets 110 of FIG. 4). Additionally, the mobile imaging device including one or more processors (e.g., CPU 402 of FIG. 2) and a controller (e.g., memory controller 468 of FIG. 2). At least one program (e.g., application 500 of FIG. 2) is non-transiently stored in the controller and executable by the controller. The at least one program causes the controller to perform the method 1300.

Block 1304. Referring to block 1304, the method 1300 includes firing the plurality of light source sets 110 with the mobile imaging device 400 held at a first position. In some embodiments, the first position is as described with respect to a corresponding first position of a method 1000 of FIG. 10. However, the present disclosure is not limited thereto. The firing is in accordance with a determination that each condition (e.g., conditions 624 of FIG. 2) in a first plurality of conditions 624 (e.g., a first subset of conditions, boundary conditions 624, etc.) satisfies a corresponding boundary condition specification. In some embodiments, the first plurality of conditions 624 is associated with a first workflow retained by the mobile imaging device 400 (e.g., workflow store 628 of FIG. 2). In this way, the mobile imaging device 400 causes the plurality of light source sets 110 to emit light that is substantially limited to a spectral range associated with the plurality of light source sets on a region of interest for a period of time. As such, this firing the plurality of light source sets 110 in accordance with the determination that each condition in the first plurality of conditions satisfies the corresponding boundary condition specification requires a computer (e.g., the mobile imaging device 400) to be used because such determinations cannot be mentally solved. In other words, given an input to determine that each condition satisfies the corresponding boundary condition specification, the output needs to be determined using a computer rather than mentally in such embodiments.

In some embodiments, the firing of the plurality of light source sets 110 of the method 1300 is as described with respect to the acquiring of the corresponding value (e.g., block 1004 of FIG. 10) and/or the firing the plurality of light source sets 110 (e.g., block 1006 of FIG. 10) of a method 1000 of FIG. 10.

Block 1306. Referring to block 1306, the method 1300 includes determining if a corresponding value for each condition 624 in a second plurality of conditions 624 satisfies a corresponding boundary condition specification based upon a plurality of measurements associated with a region of interest. The plurality of measurements is acquired using the one or more sensors of the mobile imaging device 400. For instance, in some embodiments, the plurality of measurements include at least one measurement acquired from an accelerometer (e.g., accelerometer 417 of FIG. 2) of the mobile imaging device 400, a gyroscope of the mobile imaging device 400, an objective lens of the mobile imaging device 400, a switch (e.g., switch 290 of FIG. 12) of the mobile imaging device 400, or a combination thereof. In this way, the mobile imagine device 400 can obtain a respective measurement, such as a pose of the mobile imaging device 400 from an evaluation of an image obtained by the mobile imaging device 400 or a corresponding value obtained from the one or more sensors (e.g., accelerometer 417) of the mobile imaging device 400. As such, this if determining if the corresponding value for each condition in the second plurality of conditions satisfies the corresponding boundary condition specification based upon the plurality of measurements associated with the region of interest requires a computer (e.g., the mobile imaging device 400) to be used because such determinations cannot be mentally solved. In other words, given an input to determine that each condition satisfies the corresponding boundary condition specification, the output needs to be determined using a computer rather than mentally in such embodiments.

In some embodiments, the second plurality of boundary conditions includes at least 2 boundary conditions, at least 5 boundary conditions, at least 10 boundary conditions, at least 25 boundary conditions, at least 40 boundary conditions, at least 50 boundary conditions, at least 75 boundary conditions, at least 100 boundary conditions, at least 125 boundary conditions, at least 150 boundary conditions, at least 200 boundary conditions, at least 225 boundary conditions, at least 350 boundary conditions, at least 500 boundary condition, at least 750 boundary conditions, at least 2,000 boundary conditions, at least 5,000 boundary conditions, at least 10,000 boundary conditions, at least 75,000 boundary conditions, at least 200,000 boundary conditions, at least 500,000 boundary conditions, at least $1 \times 10^6$ boundary conditions, at least $5 \times 10^6$ boundary conditions, at least $1 \times 10^7$ boundary conditions, or a combination thereof. In some embodiments, the second plurality of boundary conditions is between 10,000 and $1 \times 10^7$, between 100,000 and $5 \times 10^6$, or between 500,000 and $1 \times 10^6$.

In some embodiments, the plurality of measurements includes a distance between the mobile imaging device 400 and a portion of the region of interest. In some embodiments, the distance between the mobile imaging device 400 and the portion of the region of interest is a respective measurement of a first distance L1 of FIG. 11, a respective measurement of a second distance L2 of FIG. 11, a respective measurement of a third distance L3 of FIG. 11, a respective measurement of a fourth distance L4 of FIG. 11, or a combination thereof. However, the present disclosure is not limited thereto. In some embodiments, the distance between the mobile imaging device 400 and the region of surface includes a first distance between an upper end portion of the region of interest (e.g., an interface between an environment and a solution) and the mobile imaging device 400, a second distance between the lower end portion of the region of interest (e.g., an interface between the solution and a solid portion of the region of interest) and the mobile imaging device 400, or both. In some embodiments, the plurality of measurements includes an angle of incidence of light on the region of interest. Accordingly, the mobile imaging device 400 is capable of determining a pose of the mobile imaging device 400, a pose of the region of interest, and relative rotational and/or translational movement between the mobile imaging device 400 and the region of interest, such as a first distance between the mobile imaging device 400 and a surface of the region of interest or a second distance of a depth of the region of interest. By determining the distance between the mobile imaging device 400 and the region of interest, the mobile imaging device 400 can determine a dosage of light required to inactivate one or more organisms and generate one or more conditions 624 based on the determined distance, which ensure that a firing of the plurality of light source sets 110 emits the sufficient dosage of light to inactivate the one or more organism. In some embodiments, the distance between the mobile imaging device 400 and the region of interest is used to determine a size of the region of interest, such as a surface area of the region of interest, a volume of the region of interest, and the like. In some embodiments, the distance is determined based on a plurality of estimated positions between the mobile imaging device 400 and the region of interest, such as a first center distance, and at least two proximate distances surrounding the first center distance. Additional details and information regarding the determination of the distance is found at Gaku Nakano, 2019, "A Simple Direct Solution to the Perspective-Three-Point Problem," BMVC, pg 29, which is hereby incorporated by reference in its entirety. Specifically, in some embodiments, the pose of the mobile imaging device 400 is determined based on one or more measurements obtained from the objective lens 210, the one or more accelerometer 417, the one or more gyroscopes, or a combination thereof. Specifically, in some embodiments, the pose of the mobile imaging device 400 is determined through the objective lens 210. Additional details and information regarding the determination of the pose through an objective lens can be found at Skaloud et al., 1996, "Exterior Orientation by Direct Measurement of Camera Position and Attitude," International Archives of Photogrammetry and Remote Sensing, 31(3), print, which is hereby incorporated by reference in its entirety.

In some embodiments, the pose of the mobile imaging device 400 is determined based one or more characteristics associated with a respective region of interest. For instance, in some embodiments, one or more characteristics associated with the respective region of interest include an appearance of the region of interest (e.g., a shape of the region of interest, a color of the region of interest, a reflectance of the region of interest, etc.). In some embodiments, the one or more characteristics associated with a respective region of interest is derived from information derived from a previous firing of the plurality of light source sets 110, such as a workflow of workflow storage 628. In some embodiments, the one or more characteristics associated with a respective region of interest is based on a reference databased including a plurality of characteristics having an association with a predetermined region of interest. Additional details and information regarding determining pose based on characteristics of a region of interest can be found at Oe et al., 2005, "Estimating Camera Position and Posture by Using Feature Landmark Database," Scandinavian Conference on Image Analysis, pg. 171; Lee et al., 1998, "Fine Active Calibration of Camera Position/Orientation through Pattern Recognition," IEEE ISIE, print; Dettwiler et al., 1994, "Motion Tracking with an Active Camera," IEEE Transactions on Pattern Analysis and Machine Intelligence, 16(5), pg. 449, each of which is hereby incorporated by reference in its entirety.

In some embodiments, the plurality of measurements includes a fluence of light at a portion of the region of the interest. In some embodiments, the plurality of measurements includes an integral of the fluence and the period of time at the portion of the region of interest. For instance, in some embodiments, the integral of the fluence and the period of time at the portion of the region of interest provides a dosage of light at the portion of the region of interest. In this way, the mobile imaging device 400 can determine if an adequate dosage of light is emitted at each portion of the region of interest and/or the entire region of interest.

In some embodiments, the determining if the corresponding value of the method 1300 is performed when the acquiring of the corresponding value (e.g., block 1004 of FIG. 10) and/or the firing the plurality of light source sets 110 (e.g., block 1006 of FIG. 10) of a method 1000 of FIG. 10 is deemed complete. For instance, in some embodiments, the determining if the corresponding value of the method 1300 is performed concurrently with the firing the plurality of light source sets (e.g., block 1004 of FIG. 10, block 1304 of FIG. 13).

In some embodiments, the method 1000 of FIG. 10 and/or the method 1300 of FIG. 13 is performed with one or more models of a plurality of models of the mobile imaging device (e.g., workflow generator 630 of FIG. 2). For instance, in some embodiments, a first model is configured to acquire a corresponding value for each boundary condition in the first plurality of boundary conditions (e.g., block 1004 of FIG. 13), a second model is configured to fire the plurality of light source sets 110 (e.g., block 1006 of FIG. 10, block 1304 of FIG. 13), and a third model is configured to determine if a corresponding value for each condition in the second plurality of conditions is satisfied (e.g., block 1306 of FIG. 13). By using the plurality of classifies, the systems and methods of the present disclosure provide for a more robust firing of the plurality of light source sets 110, while ensuring the safety of a subject nearby. In some embodiments, each respective model produces a result in the plurality of model results that identifies a respective node of the plurality of nodes that best matches with a subset of data elements with a corresponding determination in a plurality of determinations in accordance with a corresponding model in the plurality of models. Said otherwise, in some embodiments, the model is implemented as an artificial intelligence engine. For instance, in some embodiments, the model includes one or more gradient boosting model, one or more random forest models, one or more neural networks (NN), one or more regression models, one or more Naïve Bayes models, one or more machine learning algorithms (MLA), or a combination thereof. In some embodiments, an MLA or a NN is trained from a training data set (e.g., a first training data set including a set of workflow from workflow storage 628 of FIG. 2) that includes one or more features identified from a data set. MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as minimum cut, harmonic function, manifold regularization, etc.), heuristic approaches, or support vector machines. In some embodiments, the supervision of a respective model is performed by an administrator associated with an entity that utilizes the systems and methods of the present disclosure.

NNs include conditional random fields, convolutional neural networks, attention based neural networks, deep learning, long short term memory networks, or other neural models.

While MLA and neural networks identify distinct approaches to machine learning, the terms may be used interchangeably herein. Thus, a mention of MLA may include a corresponding NN or a mention of NN may include a corresponding MLA unless explicitly stated otherwise. In some embodiments, the training of a respective model includes providing one or more optimized datasets, labeling these features as they occur (e.g., in user profile 16 records), and training the MLA to predict or classify based on new inputs, such as based on data captured when firing the plurality of light source sets 110. Artificial NNs are efficient computing models which have shown their strengths in solving hard problems in artificial intelligence. For instance, artificial NNs have also been shown to be universal approximators, that is, they can represent a wide variety of functions when given appropriate parameters.

Accordingly, in some embodiments, a first model is a neural network classification model, a second model is a Naïve Bayes classification model, and the like. Furthermore, in some embodiments, the model includes decision tree algorithm, a neural network algorithm, a support vector machine (SVM) algorithm, and the like. Moreover, in some embodiments, the classifier used in the (e.g., method 3400 of FIG. 34, etc.) described herein is a logistic regression algorithm, a neural network algorithm, a convolutional neural network algorithm, a support vector machine (SVM) algorithm, a Naive Bayes algorithm, a nearest neighbor algorithm, a boosted trees algorithm, a random forest algorithm, a decision tree algorithm, a clustering algorithm, or a combination thereof.

One of skill in the art will readily appreciate other models that are applicable to the systems and methods of the present disclosure. In some embodiments, the systems and methods of the present disclosure utilize more than one model to provide an evaluation (e.g., arrive at an evaluation given one or more inputs) with an increased accuracy. For instance, in some embodiments, each respective model arrives at a corresponding determination when provided a respective data set. Accordingly, each respective model can independently arrive and a result and then the result of each respective model is collectively verified through a comparison or amalgamation of the models. From this, a cumulative result is provided by the models. However, the present disclosure is not limited thereto.

In some embodiments, a respective model is tasked with performing a corresponding activity (e.g., step within method 1000 of FIG. 10, step within method 1300 of FIG. 13, etc.). In some embodiments, each respective model of the present disclosure makes use of 10 or more parameters, 100 or more parameters, 1000 or more parameters, 10,000 or more parameters, or 100,000 or more parameters. In some embodiments, each respective model of the present disclosure cannot be mentally performed.

In some embodiments, the plurality of models includes six or more models. In some embodiments, each model in the plurality of models is independently selected from the group consisting of: Naïve Bayes, decision tree, logistic regression, support vector machine, random forest, and artificial neural network. In some embodiments, a model in the plurality of models is a support vector machine, a clustering algorithm, a neural network, a decision tree, a logistic regression, a linear regression module, or a k-nearest neighbor model.

In this way, the present disclosure provides mobile imaging devices and methods at the mobile imaging devices that allow for a user to safely and effectively sterilize regions of interests. Specifically, the present disclosure provides a mobile imaging device (e.g., mobile imaging device 400 of FIG. 11) that includes a plurality of light source sets 110. In some embodiments, the plurality of light source sets 110 includes a first light source set 110-1 having at least three UV-C LED light sources and a second light source set 110-2 having one or more visible light sources. Furthermore, the mobile imaging device includes one or more sensors, preferably one or more accelerometers and a gyroscope, and a controller. The controller is non-transiently stored in the controller and executable by the controller, with at least one program causing the controller to perform the methods of the present disclosure. The methods include acquiring one or more boundary conditions 624 when the mobile imaging device 400 is at a first position. In some embodiments, the boundary conditions 624 include one or more conditions that are determined using, or require satisfying of, a plurality of measurements collected by the one or more sensors of the mobile imaging device 400. In some embodiments, the boundary conditions are associated with a region of interest, particularly when the region of interest is not exposed to UV-C irradiation. The methods include firing the plurality of light source sets 110 with the mobile imaging device 440 held at the first position in accordance with a determination that each boundary condition in the first plurality of boundary conditions is satisfied based on a plurality of firing conditions. In this way, the present disclosure acquires boundary conditions based on the first position of the mobile imaging device and ensures the boundary conditions are satisfied before emitting UV-C irradiation from the plurality of light source sets 110. Furthermore, these conditions can be based one or more prior firings of the plurality of light source sets 110 at the mobile imaging device 400, allowing for a more refined future firing of the plurality of light source sets 110. Additionally, in some embodiments, these conditions are communicated from a remote device and stored at the mobile imaging device 400, thus provide a level of remote control when firing the plurality of light source sets 110.

Thus, the present disclosure provides mobile imaging devices 400 that a user can hold and control emission of UV-C irradiation to inactivate organisms and other pathogens on surfaces of regions of interest and/or airborne organisms, at localized and/or personal level for the user. Specifically, the present disclosure allows for the mobile imaging device 400 to sterilize region of interests including airborne regions of interest, surface regions of interest, solution region of interests, or a combination thereof through the UV irradiation controlled by the mobile imaging device 400. Since the mobile imaging device 400 is operated by the individual user and controlled by conditions 624-based failsafe mechanisms, and, optionally, cross-referenced with multi-layered onboard sensor data streams obtained from the one or more sensors of the mobile imaging device 400 (e.g., the one or more gyros, one or more accelerometers, etc.) and/or from a mobile platform (e.g., client application 500, a remote device), a risk of harm is greatly reduced for the user, while also providing a mechanism for remote control of the firing of the plurality of light source sets 110. Also, in some embodiments, the mobile imaging devices 400 of the present disclosure provide low-profile emission of UV-C irradiation by configuring the plurality of light source sets 110 in a circular or rectangle array, thus providing a flexible design that can be merged with other wavelengths of light emitted from a second light source set in the plurality of light source sets 110 of the mobile imaging device. In some embodiments, the array of the plurality of light source sets 110 is a closed-formed shape, such as an n-sided polygon (n>2) closed form shaped. For instance, in some embodiments, the plurality of light source sets 110 includes an array including a first light source set 110-1 and a second light source set 110-2. In some embodiments, the array of the plurality of light source sets 110 includes a uniform distribution of the first plurality of light source sets 110-1 and the second plurality of light source sets 110-2. However, the present disclosure is not limited thereto.

Furthermore, the methods and devices of the present disclosure can provide energy coverage position progress mapped by determining one or more positions of the mobile imaging device 400 prior to and/or during the firing of the plurality of light source sets 110. Additionally, the objective lens 210 of the mobile imaging device 400 can provide imagery used for identifying characteristics of a region of interest before firing the plurality of light source sets 110, ensuring that appropriate regions of interest are irradiated with UV-C light from the plurality of light source sets 110 while unwanted regions of interest (e.g., the user) are avoided.

Additionally, the methods and devices of the present disclosure allow for remote monitoring of ancillary data streams provided from one or more objective lenses 210 of the mobile imaging device 400 and the one or more sensors of the mobile imaging device 400 (e.g., one or more gyroscopes, one or more accelerometer 417, GPS, light gate sensor, etc.) to monitor movements of the mobile imaging device 400 and view the user of the mobile imaging device 400 when firing the plurality of light source sets 110.

For convenience in explanation and accurate definition in the appended claims, the terms "upper," "lower," "up," "down," "upwards," "downwards," "inner," "outer," "inside," "outside," "inwardly," "outwardly," "interior," "exterior," "front," "rear," "back," "forwards," and "backwards" are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A method comprising:
    at a mobile imaging device comprising a plurality of light source sets, one or more sensors, a controller, and a memory, wherein at least one program is non-transiently stored in the memory and executable by the controller, the at least one program causing the controller to implement processing that includes:
    (A) acquiring, when the mobile imaging device is at a first position, a corresponding value for each boundary condition in a first plurality of boundary conditions based upon a plurality of measurements associated with a region of interest (ROI) that is not exposed to the plurality of light source sets during the acquiring, wherein the plurality of measurements is acquired using the one or more sensors; and
    (B) firing, with the mobile imaging device held at the first position, in accordance with a determination that the acquired corresponding value of each boundary condition in the first plurality of boundary conditions satisfies a corresponding boundary condition specification, the plurality of light source sets in accordance with a plurality of firing conditions, thereby emitting light that is substantially limited to a spectral range associated with the plurality of light source sets on the region of interest.

2. The method of claim 1, wherein the one or more sensors comprises a gyroscope, an accelerometer, or both.

3. The method of claim 1, wherein a first sensor in the one or more sensors comprises an objective lens in optical communication with a two-dimensional pixelated detector.

4. The method of claim 3, wherein the plurality of light source sets is distributed in an array about the objective lens.

5. The method of claim 4, wherein the array is a polygonal array or a radial array.

6. The method of claim 4, wherein a first firing condition in the plurality of firing conditions comprises a resolution of an image captured through the objective lens.

7. The method of claim 3, wherein:
    the acquiring (A) comprises acquiring a first image through the objective lens,
    the firing (B) comprises acquiring a second image through the objective lens, and
    the plurality of firing conditions comprises an evaluation of the second image based on the first image.

8. The method of claim 1, wherein a boundary condition in the first plurality of boundary conditions is a position tolerance of the mobile imaging device.

9. The method of claim 8, wherein the position tolerance of the mobile imaging device comprises one or more translational position tolerances of the mobile imaging device, one or more rotational position tolerances of the mobile imaging device, or both.

10. The method of claim 9, wherein the one or more translational position tolerances comprises a height from the ROI in a range between 3 inches and 15 inches.

11. The method of claim 8, wherein the plurality of firing conditions comprises a second position of the mobile imaging device based on the first position of the mobile imaging device.

12. The method of claim 11, wherein the second position of the mobile imaging device consists of one or more rotational positions of the mobile imaging device, a vertical translational position of the mobile imaging device, or both.

13. The method of claim 1, wherein the spectral range is in between 250 nanometers (nm) and 315 nm.

14. The method of claim 1, wherein the spectral range is in between 260 nm to 270 nm.

15. The method of claim 1, wherein the spectral range is in between 280 nm to 315 nm.

16. The method of claim 1, wherein the spectral range is in between 290 nm and 310 nm.

17. The method of claim 1, wherein the firing (B) further comprises, in accordance with a determination that the acquired corresponding value of a respective boundary condition in the plurality of boundary conditions does not satisfy the corresponding boundary condition specification, discontinuing firing of the plurality of light source sets.

18. The method of claim 1, wherein a firing condition in the plurality of firing conditions comprises an exposure time for emitting light from the plurality of lights.

19. The method of claim 18, wherein the exposure time is in between 5 seconds to 15 seconds.

20. The method of claim 18, wherein the exposure time is equal to or greater than 5 seconds.

21. The method of claim 18, wherein the exposure time provides a dosage of approximately milliJoules per square centimeter ($mJ/cm^2$), approximately 25 $mJ/cm^2$, approximately 50 $mJ/cm^2$, approximately 75 $mJ/cm^2$, approximately 100 $mJ/cm^2$, approximately 125 $mJ/cm^2$, or a combination thereof.

22. The method of claim 1, wherein the ROI comprises one or more active organisms.

23. The method of claim 1, wherein the mobile imaging device comprises a power supply powering the mobile imaging device and the plurality of light source sets.

24. The method of claim 22, wherein the one or more active organisms comprises one or more viruses, one or more bacteria, or both.

25. The method of claim 22, wherein the firing (B) causes the one or more active organisms to become inactive.

* * * * *